United States Patent
Mitani et al.

(10) Patent No.: US 9,062,024 B2
(45) Date of Patent: *Jun. 23, 2015

(54) NITROGEN-CONTAINING HETEROCYCLIC COMPOUND AND SALT THEREOF, AND A FUNGICIDE FOR AGRICULTURAL AND HORTICULTURAL USE

(75) Inventors: Akira Mitani, Naka-gun (JP); Jun Inagaki, Naka-gun (JP); Raito Kuwahara, Naka-gun (JP); Motoaki Sato, Naka-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 533 days.

This patent is subject to a terminal disclaimer.

(21) Appl. No.: 13/261,230

(22) PCT Filed: Sep. 22, 2010

(86) PCT No.: PCT/JP2010/066384
§ 371 (c)(1),
(2), (4) Date: Mar. 26, 2012

(87) PCT Pub. No.: WO2011/037128
PCT Pub. Date: Mar. 31, 2011

(65) Prior Publication Data
US 2012/0184732 A1     Jul. 19, 2012

(30) Foreign Application Priority Data

Sep. 28, 2009   (JP) ................. 2009-223525
Feb. 2, 2010    (JP) ................. 2010-021583

(51) Int. Cl.
| | |
|---|---|
| C07D 401/04 | (2006.01) |
| C07D 498/04 | (2006.01) |
| C07D 495/04 | (2006.01) |
| A01N 43/16  | (2006.01) |
| A01N 43/72  | (2006.01) |
| A01N 47/16  | (2006.01) |
| A01N 43/46  | (2006.01) |
| A01N 43/62  | (2006.01) |
| A01N 43/90  | (2006.01) |
| C07D 417/04 | (2006.01) |

(52) U.S. Cl.
CPC .............. *C07D 401/04* (2013.01); *A01N 43/46* (2013.01); *A01N 43/62* (2013.01); *A01N 43/72* (2013.01); *A01N 43/90* (2013.01); *C07D 417/04* (2013.01); *C07D 495/04* (2013.01); *C07D 498/04* (2013.01); *A01N 47/16* (2013.01)

(58) Field of Classification Search
None
See application file for complete search history.

(56) References Cited

U.S. PATENT DOCUMENTS

| | | | |
|---|---|---|---|
| 5,723,458 A | 3/1998 | Brieaddy et al. | |
| 5,817,652 A | 10/1998 | Brieaddy et al. | |
| 5,929,069 A | 7/1999 | Shudo | |
| 8,557,738 B2 * | 10/2013 | Mitani et al. ............. | 504/219 |
| 2006/0128695 A1 | 6/2006 | Bourguignon et al. | |
| 2007/0066573 A1 | 3/2007 | Albaugh et al. | |
| 2007/0173501 A1 | 7/2007 | Guo et al. | |
| 2008/0039625 A1 | 2/2008 | Lautens et al. | |
| 2008/0275242 A1 | 11/2008 | Ito et al. | |

FOREIGN PATENT DOCUMENTS

| | | |
|---|---|---|
| EP | 1736471 A1 | 12/2006 |
| JP | 07-505121 A | 6/1995 |
| JP | 08-506576 A | 7/1996 |
| JP | 08-507049 A | 7/1996 |
| JP | 09-511998 A | 12/1997 |
| JP | 10-059951 A | 3/1998 |
| JP | 2001-507341 A | 6/2001 |
| JP | 2006-507346 A | 3/2006 |
| JP | 2006-509832 A | 3/2006 |
| WO | WO 93/07131 A1 | 4/1993 |
| WO | WO 93/16999 A1 | 9/1993 |
| WO | WO 94/18183 A1 | 8/1994 |
| WO | WO 95/28399 A1 | 10/1995 |
| WO | WO 98/23617 A1 | 6/1998 |
| WO | WO 2004/041258 A2 | 5/2004 |
| WO | WO 2004/048389 A1 | 6/2004 |
| WO | WO 2005/070917 A1 | 8/2005 |
| WO | WO 2006/089298 A2 | 8/2006 |
| WO | WO 2007/011022 A1 | 1/2007 |
| WO | WO 2007/039238 A1 | 4/2007 |
| WO | WO 2008/048648 A2 | 4/2008 |
| WO | WO 2010/018686 A1 | 2/2010 |

OTHER PUBLICATIONS

Koyanagi. Synthesis and Chemistry of Agrochemicals, 1995, chapter 2, pp. 15-24.*

(Continued)

*Primary Examiner* — Noble Jarrell
(74) *Attorney, Agent, or Firm* — Foley & Lardner LLP

(57) ABSTRACT

The present invention provides a nitrogen-containing heterocyclic compound represented by formula (I) and salt thereof, which is useful as an active ingredient of a fungicide for agricultural and horticultural use, having an assured effect and being safely usable.

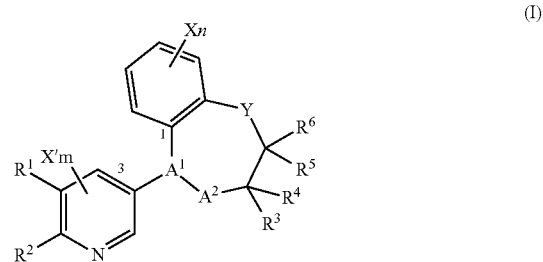

5 Claims, No Drawings

(56) References Cited

OTHER PUBLICATIONS

Saeki et al,. "Dua; Stimulatory and Inhibitory Effects of Fluorine-Substitution on Mutagenicity: An Extension of the Enamine Epoxide Theory for Activation of the Quinoline Nucleus," Biol. Pharm. Bull. 1997, 20(6):646-650.
Semple et al., "Synthesis and Biological Activity of 5-Heteroaryl Benzodiazepines: Analogues of YM022," Bioorganic & Medicinal Chemistry Letters, 1996, 6(1):55-58.
Saeki et al,. "Dual Stimulatory and Inhibitory Effects of Fluorine-Substitution on Mutagenicity: An Extension of the Enamine Epoxide Theory for Activation of the Quinoline Nucleus," Biol. Pharm. Bull, 1997, 20(6):646-650.
Archer et al., "Quinazolines and 1,4-Benzodiazepines. Part XXIX, Synthesis of Some 2,3-Dihydro-5-pyridyl-1H-1,4-benzodiazepines," Journal of the Chemical Society, Section C, Organic, 1966, 11:1031-1034.
Bock et al., "Development of 1,4-Benzodiazepine Cholecystokinin Type B Antagonists," J. Med. Chem., 1993, 36:4276-4292.
Cairns et al., "11-(Tetrahydro-3 and 4-pyridinyl)dibenzo[b,e][1,4]diazepines undergo novel rearrangements on treatment with concentrated HBr," Tetrahedron Letters, 2002, 43:1583-1585.
Escale et al., "Analogues du nor-B benzomorphane. I. Synthese des methano-3,5-tetrahydro-2,3,4,5 1H-benzazepines et derives," Journal of Heterocycl. Chemistry, 1984, 21:1033-1040.
Grunewald et al., "Effect of Ring Size or an Additional Heteroatom on the Potency and Selectivity of Bicyclic Benzylamine-Type Inhibitors of Phenylethanolamine N-Methyltranferase," J. Med. Chem., 1996, 39:3539-3546.
Haddach et al., "A New Method for the Synthesis of Ketones: The Palladium-Catalyzed Cross-Coupling of Acid Chlorides with Arylboronic Acids," Tetrahedron Letters, 1999, 40:3109-3112.
Levai et al., "Synthesis of 2,2-Dimethylbenzoxazepinones by the Schmidt Reaction of 2,2-Dimethyl-4-Chromanones," Heterocycles, 1992, 34(8):1523-1538.
Nadin et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68:2844-2852.

Saeki et al,. "Dua Stimulatory and Inhibitory Effects of Fluorine-Substitution on Mutagenicity: An Extension of the Enamine Epoxide Theory for Activation of the Quinoline Nucleus," Biol. Pharm. Bull, 1997, 20(6):646-650.
Semple et al., "Synthesis and Biological Activity of 5-Heteroaryl Benzodiazepines: Analogies of YM022," Bioorganic & Medicinal Chemistry Letters, 1996, 6(1):55-58.
Shi et al., "Method Development for a Pyridobenzodiazepine Library with Multiple Diversification Points," J. Comb. Chem., 2008, 10:158-161.
Suginome et al., "Synthesis and Helical Structure of Oligo(quinoline-2,3-diyl)s," Chemistry Lettres, 2007, 36(8):1036-1037.
Wakabayashi et al., "3-(Dimethylboryl)pyridine: Synthesis, Structure, and Remarkable Steric Effects in Scrambling Reactions," J. Org. Chem., 2008, 73:81-87.
Wu et al., "One-pot synthesis of bromodifluoroacetimidoyl halides and its Suzuki coupling reactions with aryl boronic acids," Journal of Fluorine Chemistry, 2005, 126:791-795.
Yamamoto et al., "Cyclic Triolborates: Air- and Water-Stable Ate Complexes of Organoboronic Acids," Angew. Chem. Int. Ed., 2008, 47:928-931.
Tagawa et al., "Preparation of new 3-hydroxyquinoline alkaloid, jineol and its ether derivatives using directed ortho-lithiation of chloroquinoline as the key step," Heterocycles, 1998, 48(11):2379-2387.
Supplementary European Search Report dated Oct. 10, 2011 EP 09806582.4.
International Search Report dated Sep. 8, 2009, in PCT/JP2009/003845.
Japanese Office Action dated Jul. 29, 2014, in JP 2013-112393.
Krenitsky et al., "Synthesis of the (S,S,S)-diastereomer of the 15-membered biaryl rung system of RP 66453," Tetrahedron Letters, 2003, 44:4019-4022.
Fu et al., "Synthesis of Novel Tricyclic Pyrimido[4,5,-b][1,4]benzothiazepines via Bischler-Napieralski-Type Reactions," J. Org. Chem., 2005, 70:10810-10816.
Marsais et al., "Directed ortho-Lithiation of Chloroquinolines, Application to Synthesis of 2,3-Disubstituted Quinolines," J. Heterocylic Chem., 1989, 26:1589-1594.
Tagawa et al., "Preparation of new 3-hydroxyquinoline alkaloid, jineol and its ether derivatives using directed ortho-lithiation of chloroquinone as the key step," Heterocycles, 1998, 48(11):2379-2387.

* cited by examiner

NITROGEN-CONTAINING HETEROCYCLIC COMPOUND AND SALT THEREOF, AND A FUNGICIDE FOR AGRICULTURAL AND HORTICULTURAL USE

TECHNICAL FIELD

The present invention relates to a novel nitrogen-containing heterocyclic compound and salt thereof, and a fungicide for agricultural and horticultural use including, as an active ingredient, at least one selected from nitrogen-containing heterocyclic compounds and salts thereof.

Priority is claimed on Japanese Patent Application No. 2009-223525, filed Sep. 28, 2009, and Japanese Patent Application No. 2010-021583, filed Feb. 2, 2010, the content of which is incorporated herein by reference.

BACKGROUND ART

In the cultivation of agricultural and horticultural crops, although a large number of disease control drugs are used against crop disease, since the control effects thereof may be inadequate, the use thereof may be restricted due to the appearance of drug-resistant pathogenic organisms, the plants may be damaged or contaminated by the drug, the drug may demonstrate toxicity to humans, livestock or marine life, or the drug may influence the environment, a considerable number of these control drugs are not considered to be satisfactory. Thus, there is a need to develop a plant disease control agent that can be used safely and has few of these shortcomings.

In relation to the present invention, a quinoline derivative having a chemical structure similar to the compound of the present invention, and a fungicide for agricultural and horticultural use containing the quinoline derivative as an active ingredient are disclosed in Patent Document 1 and Patent Document 2.

PRIOR ART LITERATURE

Patent Documents

Patent Document 1: WO 2005/070917
Patent Document 2: WO 2007/011022
Patent Document 3: WO 2007/039238

Non-Patent Document

Non-patent Document 1: Journal of Fluorine Chemistry 126 (2005) 791-795
Non-patent Document 2: Tetrahedro Letters 40 (1999) 3109-3112
Non-patent Document 3: Heterocycles 34 (1992) 1523-1538
Non-patent Document 4: Journal of Heterocycl. Chemistry 21 (1984) 1033-1040
Non-patent Document 5: J. Org. Chem. 73 1 (2008) 81-87
Non-patent Document 6: Chemistry Letters 36 8 (2007) 1036-1037
Non-patent Document 7: Angew. Chem. Int. Ed. 47 (2008) 928-931
Non-patent Document 8: J. Med. Chem. 39 (1996) 3539-3546
Non-patent Document 9: Biol. Pharm. Bull. 20 (1997) 646-650

DISCLOSURE OF INVENTION

Problems to be Solved by the Invention

An objective of the present invention is to provide a novel nitrogen-containing heterocyclic compound and a salt thereof, and a fungicide for agricultural and horticultural use including at least one of said compound as an active ingredient, having an assured effect and being safely useable.

Further, the present invention provides a boronic acid derivative which is an intermediate of the aforementioned compound, and a production method of the boronic acid derivative.

Means for Solving the Problems

In order to achieve the above objective, the inventors of the present invention conducted intensive investigations. As a result, the inventors of the present invention obtained a nitrogen-containing heterocyclic compound represented by formula (I) and salt thereof, and discovered that said compound or salt thereof is useful as an active ingredient of a fungicide for agricultural and horticultural use having an assured effect and being safely useable. The present invention was completed by conducting further studies on the basis of these findings.

Namely, the present invention includes the following aspects.
(1) A nitrogen-containing heterocyclic compound represented by formula (I) or salt thereof.

[Chemical formula 1]

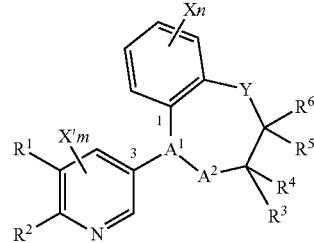

(I)

In formula (I),
$R^1$ and $R^2$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group, a cyano group or a nitro group.

$R^1$ and $R^2$ may bond to form an optionally substituted 5- to 8-membered ring together with the carbon atoms bonded thereto.

$R^3$ and $R^4$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterorcyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group.

$R^5$ and $R^6$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group.

Partial structure $A^1$-$A^2$ in formula (I) represents any one of the following formulas (A) to (D) described below:

[Chemical Formula 2]

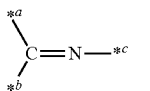
(A)

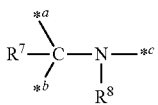
(B)

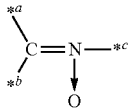
(C)

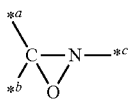
(D)

In each formula, *a represents bonding to the carbon atom at position 1 of the benzene ring;

*b represents bonding to the carbon atom at position 3 of the pyridine ring; and

*c represents bonding to the carbon atom of $CR^3R^4$.

In formula (B), $R^7$ represents a hydrogen atom, an optionally substituted C1-8 alkyl group, an optionally substituted C2-8 alkenyl group, an optionally substituted C2-8 alkynyl group, an optionally substituted C1-8 acyl group, an optionally substituted hydroxy group, an optionally substituted amino group, an optionally substituted mercapto group, a halogeno group or a cyano group.

In formula (B), $R^8$ represents a hydrogen atom, an optionally substituted C1-8 alkyl group, an optionally substituted C2-8 alkenyl group, an optionally substituted C2-8 alkynyl group or an optionally substituted C1-8 acyl group.

Y represents a sulfonyl group, a group represented by $NR^9$ or a group represented by $CR^{10}R^{11}$.

$R^9$ represents a hydrogen atom, an optionally substituted C1-8 alkyl group, an optionally substituted C2-8 alkenyl group, an optionally substituted C2-8 alkynyl group, an optionally substituted C1-8 acyl group, an optionally substituted (1-imino)C1-8 alkyl group or an optionally substituted amino group.

$R^{10}$ and $R^{11}$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group.

Here, more than one group selected from $R^3$ to $R^6$ and $R^9$ may bond to form an optionally substituted 3- to 8-membered ring together with the carbon atoms bonded thereto.

More than two groups selected from $R^3$ to $R^6$ and $R^{10}$ to $R^{11}$ may bond to form an optionally substituted 3 to 8-membered ring together with the carbons bonded thereto.

$R^3$ and $R^4$, $R^5$ and $R^6$, or $R^{10}$ and $R^{11}$ may bond to form an oxo group, a thioxo group, an optionally substituted imino group or an optionally substituted exomethylene group.

X and X' independently represent an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group, a cyano group, or a nitro group.

m represents the number of X' and represents an integer of 0 to 2.

n represents the number of X and represents an integer of 0 to 4.

(2) The nitrogen-containing heterocyclic compound or salt thereof according to (1), wherein the nitrogen-containing heterocyclic compound is represented by formula (II).

[Chemical formula 3]

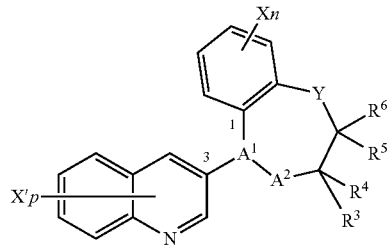
(II)

In formula (II), partial structure $A^1$-$A^2$, X, X', n, $R^3$ to $R^6$ and Y are the same as described in (1). p represents the number of X' and represents an integer of 0 to 6.

(3) The nitrogen-containing heterocyclic compound or salt thereof according to (2), wherein the nitrogen-containing heterocyclic compound is represented by formula (III).

[Chemical formula 4]

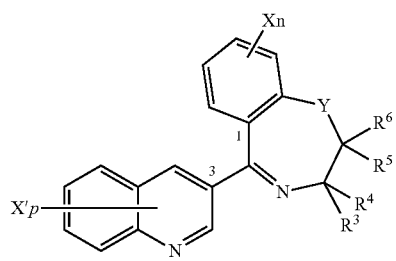
(III)

In formula (III), X, X', n, p, $R^3$ to $R^6$ and Y are the same as described in (2).

(4) A fungicide for agricultural and horticultural use, including the nitrogen-containing heterocyclic compound or salt thereof according to any one of (1) to (3) as an active ingredient.

Effects of the Invention

The nitrogen-containing heterocyclic compound or salt thereof of the present invention is a novel compound which is useful as an active ingredient of a fungicide for agricultural and horticultural use having an assured effect and being safely useable.

The fungicide for agricultural and horticultural use of the present invention has an excellent control effect without causing drug drug-related problems in plants, and demonstrates less toxicity to humans, livestock or underwater life and has less environmental impact.

Furthermore, the boronic acid derivative of the present invention is useful as an intermediate of the nitrogen-containing heterocyclic compound of the present invention or the like.

BEST MODE FOR CARRYING OUT THE INVENTION

The present invention will now be divided into 1) a nitrogen-containing heterocyclic compound represented by formulas (I) to (III) and salt thereof; 2) a production method; 3) a fungicide for agricultural and horticultural use, and be explained below in detail.

1) Nitrogen-Containing Heterocyclic Compound Represented by Formulas (I) to (III) and Salt Thereof The nitrogen-containing heterocyclic compound of the present invention (hereinafter, may be referred to as "compound of the present invention") is a compound represented by formula (I) (hereinafter, may be referred to as "compound (I)"), preferably a compound represented by formula (II) (hereinafter, may be referred to as "compound (II)"), and more preferably a compound represented by formula (III) (hereinafter, may be referred to as "compound (III)").

The nitrogen-containing heterocyclic compound or salt thereof of the present invention may include a hydrate, various solvates, crystalline polymorphism and the like. Furthermore, the nitrogen-containing heterocyclic compound or salt thereof of the present invention may include a stereoisomer based on asymmetric carbon or a double bond, or mixture thereof.

($R^1$ to $R^6$, X, and X')

In compounds (I) to (III), the groups represented by $R^1$ to $R^6$, X and X' are as follows:

$R^1$ and $R^2$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group, a cyano group, or a nitro group, preferably represent a C1-8 alkyl group or a halogeno group, and more preferably represent a C1-8 alkyl group.

$R^3$ and $R^4$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group.

$R^5$ and $R^6$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group.

Although $R^3$ to $R^6$ of the compound of the present invention may be selected from the various groups described above, a hydrogen atom or an optionally substituted C1-8 alkyl group is preferable.

X and X' independently represent an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group, a cyano group or a nitro group, preferably represent a halogeno group or a cyano group, and more preferably represent a halogeno group.

First, the meaning of "unsubstituted" and "substituted" will be explained.

The term "unsubstituted" means that a base group is the only group constituting the group. In addition, in this description, as long as there is no particular limitation, a group without modifying with "substituted" and named as a base group name means that the group is an "unsubstituted" group.

Meanwhile, the term "substituted" means that any carbon atoms constituting the base group are substituted with the following "substituent". The "substituted" group may be substituted with one substituent, or two or more substituents. The two or more substituents may be the same or different.

The term "C1-6" or the like means that the base group thereof has 1 to 6 carbon atoms. This number does not include the number of carbon atoms constituting the substituents. For example, a butyl group substituted with an ethoxy group is a C4 alkyl group.

The "substituent" is not particularly limited as long as it is chemically permissible and achieves the effects of the present invention. Examples of the "substituent" include:

a halogeno group such as a fluorine atom, chlorine atom, bromine atom, iodine atom or the like;

a C1-6 alkyl group such as a methyl group, ethyl group, n-propyl group, i-propyl group, n-butyl group, s-butyl group, i-butyl group, t-butyl group, n-pentyl group, n-hexyl group or the like;

a C3-8 cycloalkyl group such as a cyclopropyl group, cyclobutyl group, cyclopentyl group, cyclohexyl group, cycloheptyl group or the like;

a C2-6 alkenyl group such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group, cinnamyl group or the like;

a cycloalkenyl group such as a 2-cyclopropenyl group, 2-cyclopentenyl group, 3-cyclohexenyl group, 4-cyclooctenyl group or the like, preferably a C3-8 cycloalkenyl group;

a C2-6 alkynyl group such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group or the like;

a C1-6 alkoxy group such as a methoxy group, ethoxy group, n-propoxy group, i-propoxy group, n-butoxy group, s-butoxy group, i-butoxy group, t-butoxy group or the like;

a C2-6 alkenyloxy group such as a vinyloxy group, allyloxy group, propenyloxy group, butenyloxy group or the like;

a C2-6 alkynyloxy group such as an ethynyloxy group, propargyloxy group or the like;

a C6-10 aryl group such as a phenyl group, 1-naphthyl group, 2-naphthyl group or the like;

a C6-10 aryloxy group such as a phenoxy group, 1-naphthoxy group or the like;

a C7-11 aralkyl group such as a benzyl group, phenethyl group or the like;

a C7-12 aralkyloxy group such as a benzyloxy group, phenethyloxy group or the like;

a C1-7 acyl group such as a formyl group, acetyl group, propionyl group, benzoyl group, cyclohexyl carbonyl or the like;

a C1-7 acyloxy group such as a formyloxy group, acetyloxy group, propionyloxy group, benzoyloxy group, cyclohexyl carbonyloxy group or the like;

a C1-6 alkoxycarbonyl group such as a methoxycarbonyl group, ethoxycarbonyl group, n-propoxycarbonyl group, i-propoxycarbonyl group, n-butoxycarbonyl group, t-butoxycarbonyl group or the like;

a carboxyl group;

a hydroxy group;

a C1-6 haloalkyl group such as a chloromethyl group, chloroethyl group, 1,2-dichloro-n-propyl group, 1-fluoro-n-butyl group, perfluoro-n-pentyl group or the like;

a C2-6 haloalkenyl group such as a 2-chloro-1-propenyl group, 2-fluoro-1-butenyl group or the like;

a C2-6 haloalkynyl group such as a 4,4-dichloro-1-butynyl group, 4-fluoro-1-pentynyl group, 5-bromo-2-pentynyl group or the like;

a C1-6 haloalkoxy group such as a 2-chloro-n-propoxy group, 2,3-dichlorobutoxy group or the like;

a C2-6 haloalkenyloxy group such as a 2-chloropropenyloxy group, 3-bromobutenyloxy group or the like;

a C6-10 haloaryl group such as a 4-chlorophenyl group, 4-fluorophenyl group, 2,4-dichlorophenyl group or the like;

a C6-10 haloaryloxy group such as a 4-fluorophenyloxy group, 4-chloro-1-naphthoxy group or the like;

a halogen-substituted C1-7 acyl group such as a chloroacetyl group, trifluoroacetyl group, trichloroacetyl group, 4-chlorobenzoyl group or the like;

a cyano group; a nitro group; an amino group;

a C1-6 alkyl amino group such as a methyl amino group, dimethyl amino group, diethyl amino group or the like;

a C6-10 aryl amino group such as an anilino group, naphthyl amino group, anthracenyl amino group or the like;

a C7-11 aralkyl amino group such as a benzyl amino group, phenyl ethyl amino group or the like;

a C1-6 alkyl sulfonyl amino group such as a methyl sulfonyl amino group, ethyl sulfonyl amino group, n-propyl sulfonyl amino group, i-propyl sulfonyl amino group, n-butyl sulfonyl amino group, t-butyl sulfonyl amino group or the like;

a C1-7 acyl amino group such as a formyl amino group, acetyl amino group, propanoyl amino group, butyryl amino group, i-propyl carbonyl amino group, benzoyl amino group or the like;

a C1-6 alkoxycarbonyl amino group such as a methoxycarbonyl amino group, ethoxycarbonyl amino group, n-propoxycarbonyl amino group, i-propoxycarbonyl amino group or the like;

an optionally substituted aminocarbonyl group such as an aminocarbonyl group, dimethyl aminocarbonyl group, phenyl aminocarbonyl group, N-phenyl-N-methyl aminocarbonyl group or the like;

an unsubstituted or N-substituted iminoalkyl group such as an N-methyl iminomethyl group, 1-N-phenyl iminoethyl group, N-hydroxyiminomethyl group, N-methoxyiminomethyl group or the like;

a mercapto group;

a C1-6 alkyl thio group such as a methyl thio group, ethyl thio group, n-propyl thio group, i-propyl thio group, n-butyl thio group, i-butyl thio group, s-butyl thio group, t-butyl thio group or the like;

a C2-6 alkenyl thio group such as a vinyl thio group, allyl thio group or the like;

a C2-6 alkynyl thio group such as ethynyl thio group, propargyl thio group or the like;

a C6-10 aryl thio group such as a phenyl thio group, naphthyl thio group or the like;

a C1-6 alkyl sulfonyl group such as a methyl sulfonyl group, ethyl sulfonyl group, t-butyl sulfonyl group or the like;

a C2-6 alkenyl sulfonyl group such as an allyl sulfonyl group or the like;

a C2-6 alkynyl sulfonyl group such as a propargyl sulfonyl group or the like;

a C6-10 aryl sulfonyl group such as a phenyl sulfonyl group or the like;

an unsaturated 5-membered heterocyclic group such as a furan-2-yl group, furan-3-yl group, thiophene-2-yl group, thiophene-3-yl group, pyrrole-1-yl group, pyrrole-2-yl group, pyrrole-3-yl group, oxazole-2-yl group, oxazole-4-yl group, oxazole-5-yl group, thiazole-2-yl group, thiazole-4-yl group, thiazole-5-yl group, isoxazole-3-yl group, isoxazole-4-yl group, isoxazole-5-yl group, isothiazole-3-yl group, isothiazole-4-yl group, isothiazole-5-yl group, imidazole-1-yl group, imidazole-2-yl group, imidazole-4-yl group, imidazole-5-yl group, pyrazole-1-yl group, pyrazole-3-yl group, pyrazole-4-yl group, pyrazole-5-yl group, 1,3,4-oxadiazole-2-yl group, 1,3,4-thiadiazole-2-yl group, 1,2,3-triazole-4-yl group, 1,2,4-triazole-3-yl group, 1,2,4-triazole-5-yl group or the like;

an unsaturated 6-membered heterocyclic group such as a pyridine-2-yl group, pyridine-3-yl group, pyridine-4-yl group, pyridazine-3-yl group, pyridazine-4-yl group, pyrazine-2-yl group, pyrimidine-2-yl group, pyrimidine-4-yl group, pyrimidine-5-yl group, 1,3,5-triazine-2-yl group, 1,2,4-triazine-3-yl group or the like;

a saturated heterocyclic group such as a tetrahydrofuran-2-yl group, tetrahydropyran,-4-yl group, piperidine-3-yl group, pyrrolidine-2-yl group, morpholino group, piperidino group, N-methyl piperazinyl group or the like;

a heterocyclic oxy group such as a 2-pyridyloxy group, 3-oxazolyloxy group or the like;

a tri C1-6 alkyl-substituted silyl group such as a trimethyl silyl group, triethyl silyl group, t-butyl dimethyl silyl group or the like; and a triphenyl silyl group.

In addition, these "substituents" may be substituted with other "substituents".

The "C1-8 alkyl group" is a saturated hydrocarbon including 1-8 carbon atoms. The C1-8 alkyl group may be a linear alkyl group or a branched alkyl group. Examples of the C1-8 alkyl group include a methyl group, ethyl group, n-propyl group, n-butyl group, n-pentyl group, n-hexyl group, n-heptyl group, n-octyl group, i-propyl group, i-butyl group, s-butyl group, t-butyl group, i-pentyl group, neopentyl group, 2-methyl butyl group, 2,2-dimethyl propyl group, i-hexyl group or the like. Among these groups, a C1-6 alkyl group is preferable.

Examples of the "substituted C1-8 alkyl group" include a cycloalkyl alkyl group such as a cyclopropyl methyl group, 2-cyclopropyl ethyl group, cyclopentyl methyl group, 2-cyclohexyl ethyl group, 2-cyclooctyl ethyl group or the like, preferably a C3-8 cycloalkyl C1-6 alkyl group; a cycloalkenyl alkyl group such as cyclopentenyl methyl group, 3-cyclopentathenyl methyl group, 3-cyclohexenyl methyl group, 2-(3-cyclohexenyl)ethyl group or the like, preferably a C4-8 cycloalkenyl C1-6 alkyl group; a haloalkyl group such as fluoromethyl group, chloromethyl group, bromomethyl group, difluoromethyl group, dichloromethyl group, dibromomethyl group, trifluoromethyl group, trichloromethyl group, tribromomethyl group, 2,2,2-tolufluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethyl ethyl group, perfluorohexyl group, perchlorohexyl group, perfluorooctyl group, perchlorooctyl group, 2,4,6-trichlorohexyl group, perfluorodecyl group, 2,2,4,4,6,6-hexachlorooctyl group or the like, preferably a C1-6 haloalkyl group; an aryl alkyl group such as a benzyl group, phenethyl group, 3-phenyl propyl group, 1-naphthyl methyl group, 2-naphthyl methyl group or the like, preferably a C6-10 aryl C1-6 alkyl group;

a heterocyclic alkyl group such as a 2-pyridyl methyl group, 3-pyridyl methyl group, 4-pyridyl methyl group, 2-(2-pyridyl)ethyl group, 2-(3-pyridyl)ethyl group, 2-(4-pyridyl)ethyl group, 3-(2-pyridyl)propyl group, 3-(3-pyridyl)propyl group, 3-(4-pyridyl)propyl group, 2-pyrazinyl methyl group, 3-pyrazinyl methyl group, 2-(2-pyrazinyl)ethyl group, 2-(3-pyrazinyl)ethyl group, 3-(2-pyrazinyl)propyl group, 3-(3-pyrazinyl)propyl group, 2-pyrimidyl methyl group, 4-pyrimidyl methyl group, 2-(2-pyrimidyl)ethyl group, 2-(4-pyrimidyl)ethyl group, 3-(2-pyrimidyl)propyl group, 3-(4-pyrimidyl)propyl group, 2-furyl methyl group, 3-furyl methyl group, 2-(2-furyl)ethyl group, 2-(3-furyl)ethyl group, 3-(2-furyl)propyl group, 3-(3-furyl)propyl group or the like, preferably a 5- to 10-membered heterocyclic C1-6 alkyl group; a hydroxyalkyl group such as a hydroxymethyl group, hydroxyethyl group, hydroxypropyl group or the like, preferably a hydroxy C1-6 alkyl group; an alkoxyalkyl group such as a methoxymethyl group, ethoxymethyl group, methoxyethyl group, ethoxyethyl group, methoxy n-propyl group, ethoxymethyl group, ethoxyethyl group, n-propoxymethyl group, i-propoxyethyl group, s-butoxymethyl group, t-butoxyethyl group, 2,2-dimethoxyethyl group or the like, preferably a C1-6 alkoxy C1-6 alkyl group; an acyloxyalkyl group such as a formyloxymethyl group, acetoxymethyl group, 2-acetoxyethyl group, propionyloxymethyl group, propionyloxyethyl group or the like, preferably a C1-7 acyloxy C1-6 alkyl group; or the like.

The "C2-8 alkenyl group" is an unsaturated hydrocarbon group including 2-8 carbon atoms and having at least one double bond of C to C. The C2-8 alkenyl group may be a linear alkenyl group or a branched alkenyl group. Examples of the C2-8 alkenyl group include a vinyl group, 1-propenyl group, allyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-heptenyl group, 6-heptenyl group, 1-octenyl group, 7-octenyl group, 1-methyl-2-propenyl group, 2-methyl-2-propenyl group, 1-methyl-2-butenyl group, 2-methyl-2-butenyl group or the like. Among these groups, a C2-6 alkenyl group is preferable.

Examples of the "substituted C2-8 alkenyl group" include a haloalkenyl group such as a 3-chloro-2-propenyl group, 4-chloro-2-butenyl group, 4,4-dichloro-3-butenyl group, 4,4-difluoro-3-butenyl group, 3,3-dichloro-2-propenyl group, 2,3-dichloro-2-propenyl group, 3,3-difluoro-2-propenyl group, 2,4,6-trichloro-2-hexenyl group or the like; preferably a C2-6 alkenyl group substituted with 1 to 3 halogen atoms.

The "C2-8 alkynyl group" is an unsaturated hydrocarbon group including 2-8 carbon atoms and having at least one triple bond of C to C. The C2-8 alkynyl group may be a linear alkyneyl group or a branched alkyneyl group. Examples of the C2-8 alkynyl group include an ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1-hexynyl group, 1-methyl-2-propynyl group, 2-methyl-3-butynyl group, 1-methyl-2-butynyl group, 2-methyl-3-pentynyl group, 1,1-dimethyl-2-butynyl group or the like. Among these groups, a C2-6 alkynyl group is preferable.

Examples of the "substituted C2-8 alkynyl group" include a haloalkynyl group such as a 3-chloro-1-propynyl group, 3-chloro-1-butynyl group, 3-bromo-1-butynyl group, 3-bromo-2-propynyl group, 3-iodo-2-propynyl group, 3-bromo-1-hexynyl group, 5,5-dichloro-2-methyl-3-pentynyl group, 4-chloro-1,1-dimethyl-2-butynyl group or the like, preferably a C2-6 alkynyl group substituted with 1 to 3 halogen atoms.

The "C3-8 cycloalkyl group" is an alkyl group including 3-8 carbon atoms and having a cyclic moiety. Examples of the C3-8 cycloalkyl group include a cyclopropyl group, cyclobutyl group, cyclopentyl group, cyclohexyl group, cycloheptyl group, cyclooctyl group or the like. Among these groups, a C3-6 cycloalkyl group is preferable.

Examples of the "substituted C3-8 cycloalkyl group" include an alkyl cycloalkyl group such as a 2,3,3-trimethyl cyclobutyl group, 4,4,6,6-tetramethyl cyclohexyl group, 1,3-dibutyl cyclohexyl group or the like, preferably a C3-8 cycloalkyl group substituted with 1 to 3 C1-6 alkyl groups or the like.

The "C4-8 cycloalkenyl group" is an alkenyl group including 4-8 carbon atoms and having a cyclic moiety. Examples of the C4-8 cycloalkenyl group include a 1-cyclobutenyl group, 1-cyclopentenyl group, 3-cyclopentenyl group, 1-cyclohexenyl group, 3-cyclohexenyl group, 3-cycloheptenyl group, 4-cyclooctenyl group or the like.

Examples of the "substituted C4-8 cycloalkenyl group" include an alkyl cycloalkenyl group such as a 2-methyl-3-cyclohexenyl group, 3,4-dimethyl-3-cyclohexenyl group or the like, preferably a C4-8 cycloalkenyl group substituted with 1 to 3 C1-6 alkyl groups.

The "C6-10 aryl group" is an aryl group including 6-10 carbon atoms and having a monocyclic moiety or a polycyclic moiety. In addition, in the polycyclic aryl group, as long as at least one ring is an aromatic ring, other rings may be a saturated alicyclic ring, an unsaturated alicyclic ring or an aromatic ring. Examples of the C6-10 aryl group include a phenyl group, naphthyl group, azulenyl group, indenyl group, indanyl group, tetralinyl group or the like. Among these groups, a phenyl group is preferable.

The "heterocyclic group" indicates a 3- to 7-membered heteroaromatic ring, a 3- to 7-membered saturated heterocyclic ring or a 3- to 7-membered unsaturated heterocyclic ring having 1 to 4 hetero atoms selected from a nitrogen atom, oxygen atom and sulfur atom other than a carbon atom as an atom constituting the ring, or indicates a 9- to 10-membered condensed heterocyclic ring in which the benzene ring and the heterocyclic ring are condensed.

Examples of the heterocyclic group include a pyrrol-1-yl group, pyrrol-2-yl group, pyrrol-3-yl group, furan-2-yl group, furan-3-yl group, thiophene-2-yl group, thiophene-3-yl group, imidazole-1-yl group, imidazole-2-yl group, imidazole-4-yl group, imidazole-5-yl group, pyrazole-1-yl group, pyrazole-3-yl group, pyrazole-4-yl group, pyrazole-5-yl group, oxazole-2-yl group, oxazole-4-yl group, oxazole-5-yl group, thiazole-2-yl group, thiazole-4-yl group, thiazole-5-yl group, isoxazole-3-yl group, isoxazole-4-yl group, isoxazole-5-yl group, isothiazole-3-yl group, isothiazole-4-yl group, isothiazole-5-yl group, 1,2,3-triazole-1-yl group, 1,2,3-triazole-4-yl group, 1,2,3-triazole-5-yl group, 1,2,4-triazole-1-yl group, 1,2,4-triazole-3-yl group, 1,2,4-triazole-5-yl group, 1,3,4-oxadiazole-2-yl group, 1,2,4-oxadiazole-3-yl group, 1,3,4-thiadiazole-2-yl group, 1,2,4-thiadiazole-3-yl group, tetrazole-1-yl group, tetrazole-2-yl group; pyridine-2-yl group, pyridine-3-yl group, pyridine-4-yl group, pyrazine-2-yl group, pyrimidine-2-yl group, pyrimidine-4-yl group, pyrimidine-5-yl group, pyridazine-3-yl group, pyridazine-4-yl group, triazinyl group;

indole-1-yl group, indole-2-yl group, indole-3-yl group, indole-4-yl group, indole-5-yl group, indole-6-yl group, indole-7-yl group, benzofuran-2-yl group, benzofuran-3-yl group, benzofuran-4-yl group, benzofuran-5-yl group, benzofuran-6-yl group, benzofuran-7-yl group, benzothiophene-2-yl group, benzothiophene-3-yl group, benzothiophene-4-yl group, benzothiophene-5-yl group, benzothiophene-6-yl group, benzothiophene-7-yl group, isoindole-1-yl group, isoindole-2-yl group, isoindole-4-yl group, isoindole-5-yl group, isoindole-6-yl group, isoindole-7-yl group, isobenzofuran-1-yl group, isobenzofuran-4-yl group, isobenzofuran-5-yl group, isobenzofuran-6-yl group, isobenzofuran-7-yl group, benzimidazole-1-yl group, benzimidazole-2-yl group, benzimidazole-4-yl group, benzimidazole-5-yl group, benzoxazole-2-yl group, benzoxazole-4-yl group, benzoxazole-5-yl group, benzothiazole-2-yl group, benzothiazole-4-yl group, benzothiazole-5-yl group; chromene-2-yl group, chromene-3-yl group, chromene-4-yl group, chromene-5-yl group, chromene-6-yl group, chromene-7-yl group, chromene-8-yl group, quinoline-2-yl group, quinoline-3-yl group, quinoline-4-yl group, quinoline-5-yl group, quinoline-6-yl group, quinoline-7-yl group, quinoline-8-yl group, isoquinoline-1-yl group, isoquinoline-3-yl group, isoquinoline-4-yl group, isoquinoline-5-yl group, isoquinoline-6-yl group, isoquinoline-7-yl group, isoquinoline-8-yl group;

aziridine-1-yl group, aziridine-2-yl group, epoxy group; pyrrolidine-1-yl group, pyrrolidine-2-yl group, pyrrolidine-3-yl group, tetrahydrofuran-2-yl group, tetrahydrofuran-3-yl group; piperidine-1-yl group, piperidine-2-yl group, piperidine-3-yl group, piperidine-4-yl group, piperazine-1-yl group, piperazine-2-yl group, piperazine-3-yl group, morpholine-2-yl group, morpholine-3-yl group, morpholine-4-yl group;

1,3-benzodioxole-4-yl group, 1,3-benzodioxole-5-yl group, 1,4-benzodioxane-5-yl group, 1,4-benzodioxane-6-yl group, 3,4-dihydro-2H-1,5-benzodioxepine-6-yl group, 3,4-dihydro-2H-1,5-benzodioxepine-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group; or the like.

Among these groups, a 5- to 10-membered heterocyclic group is preferable.

The "C1-8 acyl group" is a group in which a hydrogen atom, a C1-7 alkyl group, a C2-7 alkenyl group, a C2-7 alkynyl group, phenyl group or a 5- to 7-membered heterocyclic group bonds to a carbonyl group.

Examples of the C1-8 acyl group include a formyl group, acetyl group, propionyl group, an alkyl carbonyl group such as an n-propyl carbonyl group, n-butyl carbonyl group, pentanoyl group, valeryl group, octanoyl group, i-propyl carbonyl group, i-butyl carbonyl group, pivaloyl group, i-valeryl group or the like; an alkenyl carbonyl group such as an acryloyl group, methacryloyl group or the like; an alkynyl carbonyl group such as a propioloyl group or the like; an aryl carbonyl group such as a benzoyl group or the like; a heterocyclic carbonyl group such as a 2-pyridyl carbonyl group, thienyl carbonyl group or the like; or the like. Among these groups, a C1-7 acyl group is preferable.

Examples of the "substituted C1-8 acyl group" include a C1-8 acyl group substituted with halogen atoms such as a monofluoroacetyl group, monochloroacetyl group, monobromoacetyl group, difluoroacetyl group, dichloroacetyl group, dibromoacetyl group, trifluoroacetyl group, trichloroacetyl group, tribromoacetyl group, 3,3,3-trifluoropropionyl group, 3,3,3-trichloropropionyl group, 2,2,3,3,3-pentafluoropropionyl group or the like, preferably a C1-7 acyl group substituted with 1 to 3 halogen atoms; a carboxyl group; a methoxycarbonyl group, ethoxycarbonyl group, n-propoxycarbonyl group, i-propoxycarbonyl group, n-butoxycarbonyl group, i-butoxycarbonyl group, t-butoxycarbonyl group, n-pentyloxycarbonyl group, n-hexyloxycarbonyl group; a C1-7 alkoxycarbonyl group such as a cyclopropyl methyloxycarbonyl group, 2-cyclopentyl ethyloxycarbonyl group, benzyloxycarbonyl group or the like; carbamoyl group; a mono C1-6 alkyl carbamoyl group or a di C1-6 alkyl carbamoyl group such as a methyl carbamoyl group, ethyl carbamoyl group, dimethyl carbamoyl group, diethyl carbamoyl group or the like, a monoaryl carbamoyl group such as a phenyl carbamoyl group, 4-methyl phenyl carbamoyl group or the like, preferably a mono C6-10 aryl carbamoyl group; an acyl carbamoyl group such as an acetyl carbamoyl group, benzoyl carbamoyl group or the like, preferably a C1-7 acyl carbamoyl group or the like.

The "(1-imino)C1-8 alkyl group" is an iminomethyl group or a group in which a C1-7 alkyl group bonds to an iminomethyl group. Examples of the (1-imino)C1-8 alkyl group include an iminomethyl group, (1-imino)ethyl group, (1-imino)propyl group, (1-imino)butyl group, (1-imino)pentyl group, (1-imino)hexyl group, (1-imino)heptyl group or the like. Among these groups, a (1-imino)C1-6 alkyl group is preferable.

Examples of the "substituted (1-imino)C1-8 alkyl group" include a (1-hydroxyimino)C1-8 alkyl group such as a hydroxyiminomethyl group, (1-hydroxyimino)ethyl group, (1-hydroxyimino)propyl group, (1-hydroxyimino)butyl group or the like, preferably a (1-hydroxyimino)C1-6 alkyl group; a (1-(C1-6 alkoxy)imino)C1-6 alkyl group such as a methoxyiminomethyl group, (1-ethoxyimino)methyl group, (1-ethoxyimino)ethyl group or the like; or the like.

Examples of the "substituted amino group" include a mono C1-6 alkyl amino group or a di C1-6 alkyl amino group such as a methyl amino group, ethyl amino group, dimethyl amino group, diethyl amino group or the like; a mono C1-6 alkylidene amino group such as a methylidene amino group, ethylidene amino group or the like; a monoaryl amino group such as a phenyl amino group, 4-methyl phenyl amino group or the like, preferably a mono C6-10 aryl amino group; a diaryl amino group such as a di 1-naphthyl amino group or the like, preferably a di C6-10 aryl amino group; an acyl amino group acetyl amino group, benzoyl amino group or the like, preferably a C1-7 acyl amino group; or the like.

Examples of the "substituted hydroxy group" include an alkoxy group such as a methoxy group, ethoxy group, n-propoxy group, n-butoxy group, n-pentyloxy group, n-hexyloxy group, i-propoxy group, i-butoxy group, s-butoxy group, t-butoxy group, 1-ethyl propoxy group, i-hexyloxy group, 4-methyl pentoxy group, 3-methyl pentoxy group, 2-methyl pentoxy group, 1-methyl pentoxy group, 3,3-dimethyl butoxy group, 2,2-dimethyl butoxy group, 1,1-dimethyl butoxy group, 1,2-dimethyl butoxy group, 1,3-dimethyl butoxy group, 2,3-dimethyl butoxy group, 1-ethyl butoxy group, 2-ethyl butoxy group or the like, preferably a C1-7 alkoxy group; cyclopropyl methyloxy group, 2-cyclopentyl ethyloxy group, benzyloxy group; a C1-6 alkoxy group substituted with 1 to 3 hologen atoms such as a chloromethoxy group, dichloromethoxy group, trichloromethoxy group, trifluoromethoxy group, 1-fluoroethoxy group, 1,1-difluoroethoxy group, 2,2,2-trifluoroethoxy group, pentafluoroethoxy group or the like;

a C2-8 alkenyloxy group such as a vinyloxy group, 1-propenyloxy group, 2-propenyloxy group, 1-butenyloxy group, 2-butenyloxy group, 3-butenyloxy group, 1-pentenyloxy group, 2-pentenyloxy group, 3-pentenyloxy group, 4-pentenyloxy group, 1-hexenyloxy group, 2-hexenyloxy group, 3-hexenyloxy group, 4-hexenyloxy group, 5-hexenyloxy group, 1-heptenyloxy group, 6-heptenyloxy group, 1-octenyloxy group, 7-octenyloxy group, 1-methyl-2-propenyloxy group, 2-methyl-2-propenyloxy group, 1-methyl-2-butenyloxy group, 2-methyl-2-butenyloxy group or the like, preferably a C2-6 alkenyloxy group; an alkynyloxy group such as an ethynyloxy group, propynyloxy group, propargyloxy group, 1-butynyloxy group, 2-butynyloxy group, 3-butynyloxy group, 1-pentynyloxy group, 2-pentynyloxy group, 3-pentynyloxy group, 4-pentynyloxy group, 1-hexynyloxy group, dodecynyloxy group, butadecynyloxy group, heptadecynyloxy group, 1-methyl-2-propynyloxy group, 2-methyl-3-butynyloxy group, 1-methyl-2-butynyloxy group, 2-methyl-3-pentynyloxy group, 1,1-dimethyl-2-butynyloxy group, 4-ethyl hexadecynyloxy group or the like, preferably a C2-6 alkynyloxy group; a cyclopropyloxy group, cyclobutyloxy group, cyclopentyloxy group, cyclohexyloxy group, cycloheptyloxy group, cyclooctyloxy group;

a C3-8 cycloalkoxy group such as a 2-methyl cyclopropyloxy group, 2-ethyl cyclopropyloxy group, 2,3,3-trimethyl cyclobutyloxy group, 2-methyl cyclopentyloxy group, 2-ethyl cyclohexyloxy group, 2-ethyl cyclooctyloxy group, 4,4,6,6-tetramethyl cyclohexyloxy group, 1,3-dibutyl cyclohexyloxy group or the like, preferably a C3-6 cycloalkoxy group; a C6-10 aryloxy group such as a phenyloxy group, naphthyloxy group, azulenyloxy group, indenyloxy group, indanyloxy group, tetralinyloxy group or the like, preferably a C6-10 aryloxy group; a C1-8 acyloxy group such as an acetyloxy group, propionyloxy group, n-propyl carbonyloxy group, i-propyl carbonyloxy group, n-butyl carbonyloxy group, i-butyl carbonyloxy group, pentanoyloxy group, pivaloyloxy group or the like, preferably a C1-7 acyloxy group; or the like.

Examples of the "substituted mercapto group" include a C1-6 alkyl thio group such as a methyl thio group, ethyl thio group or the like; an aryl thio group such as a phenyl thio group, 4-methyl phenyl thio group or the like, preferably a C6-10 aryl thio group; an acyl thio group such as an acetyl thio group, benzoyl thio group or the like, preferably a C1-7 acyl thio group; or the like.

Examples of the "halogeno group" include a fluorine atom, chlorine atom, bromine atom, iodine atom and the like.

Examples of the "substituted sulfonyl group" include a C1-6 alkyl sulfonyl group such as a methyl sulfonyl group, ethyl sulfonyl group, n-propyl sulfonyl group, i-propyl sulfonyl group, n-butyl sulfonyl group, i-butyl sulfonyl group, s-butyl sulfonyl group, t-butyl sulfonyl group, n-pentyl sulfonyl group, i-pentyl sulfonyl group, neopentyl sulfonyl group, 1-ethyl propyl sulfonyl group, n-hexyl sulfonyl group, i-hexyl sulfonyl group and the like; a haloalkyl sulfonyl group such as a trifluoromethyl sulfonyl group or the like, preferably a C1-6 haloalkyl sulfonyl group; an aryl sulfonyl group such as a phenyl sulfonyl group, 4-methyl phenyl sulfonyl group or the like, preferably a C6-10 aryl sulfonyl group; sulfo group; an alkoxysulfonyl group such as a methoxysulfonyl group, ethoxysulfonyl group or the like, preferably a C1-6 alkoxysulfonyl group; sulfamoyl group; a sulfamoyl group such as an N-methyl sulfamoyl group, N-ethyl sulfamoyl group, N,N-dimethyl sulfamoyl group, N,N-diethyl sulfamoyl group or the like, preferably a mono C1-6 alkyl sulfamoyl group or a di C1-6 alkyl sulfamoyl group; a monoaryl sulfamoyl group such as a phenyl sulfamoyl group, 4-methyl phenyl sulfamoyl group or the like, preferably a mono C6-10 aryl sulfamoyl group or the like.

In the compound of the present invention, although X and X' may be selected from the various groups as described above, a halogen atom is preferable. m represents the number of X', and may be any one of integers of 0 to 2. n represents the number of X, and may be any one of integers of 0 to 4.

(Y)

In the present invention, Y represents a sulfonyl group, a group represented by $NR^9$ or a group represented by $CR^{10}R^{11}$.

In the present invention, examples of $R^9$ include a hydrogen atom, an optionally substituted C1-8 alkyl group, an optionally substituted C2-8 alkenyl group, an optionally substituted C2-8 alkynyl group, an optionally substituted C1-8 acyl group, an optionally substituted (1-imino)C1-8 alkyl group or an optionally substituted amino group, preferably a hydrogen atom, an optionally substituted C1-8 alkyl group, an optionally substituted C2-8 alkenyl group and an optionally substituted C1-8 acyl group. Examples of the optionally substituted C1-8 alkyl group, the optionally substituted C2-8 alkenyl group, the optionally substituted C2-8 alkynyl group, the optionally substituted C1-8 acyl group, the optionally substituted (1-imino)C1-8 alkyl group and the optionally substituted amino group of $R^9$ are the same as the examples of $R^1$ to $R^6$, X and X'.

Examples of the "substituted C1-8 alkyl group" include a C1-8 alkyl group having a C6-10 aryl group, and the like. Examples of the "substituted C1-8 acyl group" include a C1-8 acyl group substituted with a halogen atom, a C1-7 alkoxycarbonyl group and the like.

In the compound of the present invention, examples of $R^{10}$ and $R^{11}$ include a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group and a cyano group, preferably a hydrogen atom and an optionally substituted C1-8 alkyl group.

Examples of the optionally substituted C1-8 alkyl group, the optionally substituted C2-8 alkenyl group, the optionally substituted C2-8 alkynyl group, the optionally substituted C3-8 cycloalkyl group, the optionally substituted C4-8 cycloalkenyl group, the optionally substituted C6-10 aryl group, the optionally substituted heterocyclic group, an optionally substituted C1-8 acyl group, the optionally substituted (1-imino)C1-8 alkyl group, the optionally substituted hydroxy group, the optionally substituted amino group, the optionally substituted mercapto group, the substituted sulfonyl group and the halogeno group of $R^{10}$ and $R^{11}$ are the same as the examples of $R^1$ to $R^6$, X and X'.

(5- to 8-Membered Ring Formed by Bonding $R^1$ and $R^2$)

In the compound of the present invention, examples of the optionally substituted 5- to 8-membered ring formed by bonding $R^1$ and $R^2$ together with the hydrogen atoms bonded thereto include an aromatic hydrocarbon ring such as a benzene ring or the like; an aromatic hetero ring such as a furan ring, thiophene ring, pyrrole ring, pyridine ring, pyrazine ring, pyrimidine ring, pyridazine ring, imidazole ring, pyrazole ring, thiazole ring, oxazole ring, isoxazole ring or the like; an aliphatic hydrocarbon ring such as a cycloalkene ring such as a cyclopentene ring, cyclohexene ring, cycloheptene ring, cyclooctene ring or the like; an unsaturated hetero ring such as a dihydro-2H-pyran ring, dihydro-2H-thiopyran ring, tetrahydropyridine ring or the like.

In the compound of the present invention, among these groups, a benzene ring is preferable. Namely, an unsubstituted benzene ring or a benzene ring substituted with a halogeno group is preferable.

(Group Formed by Bonding $R^3$-$R^6$ or the Like)

In the composition of the present invention, examples of the "substituted imino group" formed by bonding $R^3$ and $R^4$, $R^5$ and $R^6$ or $R^{10}$ and $R^{11}$ include a methyl imino group, benzyl imino group; a hydroxyimino group, ethoxyimino group or the like.

Examples of the "substituted exomethylene group" formed by bonding $R^3$ and $R^4$, $R^5$ and $R^6$ or $R^{10}$ and $R^{11}$ include a methylene group, ethylidene group or the like.

Examples of the "optionally substituted 3- to 8-membered ring formed by bonding more than one group selected from $R^3$ to $R^6$ and $R^9$ together with the hydrogen atome bonded thereto" include an aliphatic hydrocarbon ring such as a cycloalkane ring such as a cyclopropane ring, cyclopentane ring, cyclohexane ring, cycloheptane ring, cyclooctane ring or the like; a benzene ring or the like; an aromatic hetero ring such as a furan ring, thiophene ring, pyrrole ring, pyridine ring, pyrazine ring, pyrimidine ring, pyridazine ring, imidazole ring, pyrazole ring, triazole ring, tetrazole ring, thiazole ring, oxazole ring, isoxazole ring or the like; an unsaturated hetero ring such as a dihydro-2H-pyran ring, dihydro-2H-thiopyran ring, tetrahydropyridine ring or the like.

Examples of the "optionally substituted 3- to 8-membered ring formed by bonding more than one group selected from $R^3$ to $R^6$ and $R^{10}$ to $R^{11}$ together with the hydrogen atoms bonded thereto" include an aliphatic hydrocarbon ring such as a cycloalkane ring such as a cyclopropane ring, cyclopentane ring, cyclohexane ring, cycloheptane ring, cyclooctane ring or the like; an aromatic hydrocarbon ring such as a benzene ring or the like; an aromatic hetero ring such as a furan ring, thiophene ring, pyrrol ring, pyridine ring, pyrazine ring, pyrimidine ring, pyridazine ring, imidazole ring, pyrazole ring, triazole ring, tetrazole ring, thiazole ring, oxazole ring, isoxazole ring or the like; an unsaturated hetero ring such as a dihydro-2H-pyran ring, dihydro-2H-thiopyran ring, tetrahydropyridine ring or the like.

In the compound of the present invention, the group formed by bonding $R^{10}$ and $R^{11}$ is preferably an oxogroup.

($A^1$-$A^2$)

Partial structure $A^1$-$A^2$ represents the following formulas (A) to (D).

[Chemical formula 5]

(A)

(B)

(C)

(D)

In each formula, *a represents bonding to the carbon atom at position 1 of the benzene ring.

*b represents bonding to the carbon atom at position 3 of the pyridine ring.

*c represents bonding to the carbon atom of $CR^3R^4$.

In formula (B), $R^7$ represents a hydrogen atom, an optionally substituted C1-8 alkyl group, an optionally substituted C2-8 alkenyl group, an optionally substituted C2-8 alkynyl group, an optionally substituted C1-8 acyl group, an optionally substituted hydroxy group, an optionally substituted amino group, an optionally substituted mercapto group, a halogeno group or a cyano group. In the compound of the present invention, $R^7$ is preferably a hydrogen atom. Examples of the optionally substituted C1-8 alkyl group, the optionally substituted C2-8 alkenyl group, the optionally substituted C2-8 alkynyl group, the optionally substituted C1-8 acyl group, the optionally substituted hydroxy group, the optionally substituted amino group, the optionally substituted mercapto group and the halogeno group of $R^7$ are the same as the examples of $R^1$ to $R^6$, X and X'.

In formula (B), $R^8$ represents a hydrogen atom, an optionally substituted C1-8 alkyl group, an optionally substituted C2-8 alkenyl group, an optionally substituted C2-8 alkynyl group or an optionally substituted C1-8 acyl group. In the compound of the present invention, $R^8$ is preferably a hydrogen atom. Examples of the optionally substituted C1-8 alkyl group, the optionally substituted C2-8 alkenyl group, the optionally substituted C2-8 alkynyl group or the optionally substituted C1-8 acyl group of $R^8$ are the same as the examples of $R^1$ to $R^6$, X, and X'.

In the compound of the present invention, the partial structure $A^1$-$A^2$ is preferably represented by formula (A), namely, C=N (imine).

(Compound (II))

In the compound of the present invention, the optionally substituted 5- to 8-membered ring formed by bonding $R^1$ and $R^2$ together with the carbon atoms bonded thereto is preferably a benzene ring. Namely, the compound of the present invention is preferably compound (II).

p represents the number of X', and preferably is an integer of 0 to 6, and more preferably an integer of 0 to 2.

(Compound (III))

Furthermore, in the compound of the present invention, partial structure $A^1$-$A^2$ is preferably represented by formula (A), specifically, C=N (imine). Namely, the compound of the present invention is preferably compound (III).

(Salt of the Compound)

There are no particular limitations on the salts of the compound of the present invention provided it is an agriculturally and horticulturally allowable salt. Examples of the salt include salts of inorganic acids such as hydrochloric acid or sulfuric acid; salts of organic acids such as acetic acid or lactic acid; salts of alkaline metals such as lithium, sodium or potassium; salts of alkaline earth metals such as calcium or magnesium; salts of transition metals such as iron or copper; and, salts of organic bases such as ammonia, triethylamine, tributylamine, pyridine or hydrazine.

2) Production Method of the Compound of the Present Invention

The compound of the present invention can be produced according to a known method. For example, a compound represented by the following formula (1) can be prepared by a Suzuki coupling reaction between a boronic acid derivative represented by the following formula (2) and an imidoyl halide derivative represented by the following formula (3) using a palladium complex described in the aforementioned Non-Patent Document 1 or Non-Patent Document 2.

Here, a boronic acid derivative represented by the following formula (2') may be used instead of the boronic acid derivative represented by formula (2):

[Chemical formula 6]

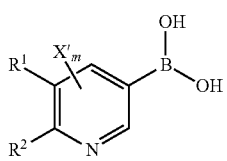

(2)

[Chemical 7]

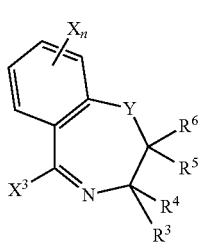

(3)

[Chemical formula 8]

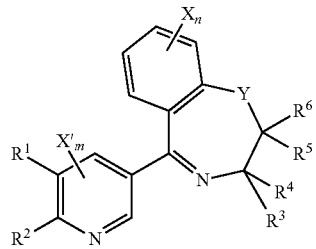

(1)

(in the formula, $R^1$ to $R^6$, X, X', Y, n, m are the same as defined above. $X^3$ represents a halogen atom.)

[Chemical formula 9]

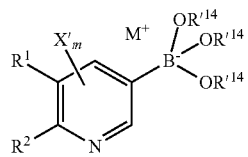

(2')

(in the formula, $R^1$, $R^2$, X', m are the same as defined above. $R'^{14}$ represents a C1-8 alkyl group. M represents an alkaline metal such as lithium, sodium or potassium.)

[Chemical formula 10]

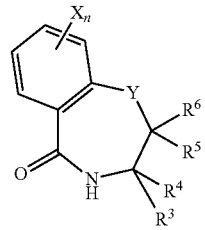

(4)

A compound represented by formula (3) can be prepared by a method in which a cyclic amide represented by formula (4) reacts in the presence of an acid halide such as phosgene, oxalyl chloride or thionyl chloride. In addition, the reaction of triphenylphosphine and carbon tetrachloride may also be used to obtain the compound.

[Chemical formula 11]

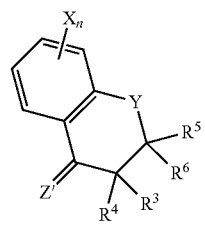

(5)

(in the formula, $R^3$ to $R^6$, X, Y, n are the same as defined above. Z' represents an oxygen atom or N—OH.)

A compound represented by formula (4) can be prepared by carrying out a Schmidt reaction of a cyclic acetophenone derivative represented by formula (5), or by carrying out a Beckmann rearrangement after deriving an oxime from a cyclic acetophenone derivative represented by formula (5). Various modified procedures have been reported for the two reactions.

The Schmidt reaction can be carried out by reacting a ketone in sodium azide and a strong acid, such as concentrated hydrochloric acid, sulfuric acid, trifluoroacetic acid methanesulfonic acid or the like in the absence of a solvent, or in the presence of a solvent such as acetonitrile, chloroform or methylene chloride, as described in Non-Patent Document 3 or Non-Patent Document 4.

In the Beckmann rearrangement, an oxime of a carbonyl compound reacts with polyphosphoric acid or a trimethylsilyl ester thereof, or an oxime of a carbonyl compound reacts at a high temperature in the presence of a Lewis acid such as aluminum triiodide or iron (III) chloride-impregnated montmorillonite in the absence of a solvent or in the presence of a solvent such as acetonitrile. In addition, the compound represented by formula (4) may also be prepared by forming a mesylate or tosylate of an oxime followed by treating with a base such as aqueous sodium hydroxide solution or treating with a Lewis acid such as diethyl aluminum chloride.

The oxime can be prepared using a known method. For example, it can be produced by reacting an acetophenone derivative with a hydroxylamine hydrochloride in a solvent such as ethanol, followed by adding a base such as pyridine, sodium acetate or aqueous sodium hydroxide solution as necessary at a temperature up to the boiling point of the solvent.

In addition, a compound represented by formula (1') can be prepared by (i) a contact hydrogenation method in which a compound represented by formula (1) reacts with hydrogen in the presence of a contact reduction catalyst such as palladium-carbon, platinum oxide or Raney nickel and hydrogen, or by (ii) a method in which a compound represented by formula (1) is reduced in the presence of a metal-hydrogen compound such as lithium aluminum hydride or sodium borohydride.

[Chemical formula 12]

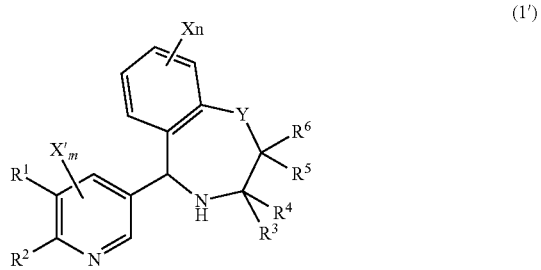

(1')

(in the formula, $R^1$ to $R^6$, X, X', Y, n, m are the same as defined above.)

(Production Method of Intermediate)

A production method of an intermediate of the compound of the present invention will be explained.

a C1-6 alkyl magnesium halide reacts with a C1-6 alkyl lithium, followed by reaction with a compound represented by formula (VI):

[Chemical formula 13]

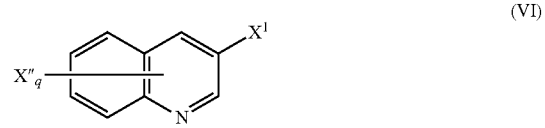

(VI)

In formula (VI), X" independently represents an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted hydroxy group, an optionally substituted amino group, an optionally substituted mercapto group, a fluorine atom, a chlorine atom or a nitro group.

Examples of X" are the same as the examples of the "group" described in the explanation of formula (I).

q represents any one of integers of 0 to 6. $X^1$ represents a bromine atom or an iodine atom.

Examples of the C1-6 alkyl magnesium halide used for the production of intermediate include methyl magnesium chloride, ethyl magnesium chloride, n-propyl magnesium chloride, n-butyl magnesium chloride, s-butyl magnesium chloride, t-butyl magnesium chloride, n-butyl magnesium bromide, n-butyl magnesium iodide and the like. These compounds can be used alone or in combination of two or more compounds. Among these compounds, n-butyl magnesium chloride is preferable.

Examples of the C1-6 alkyl lithium used for the production of the intermediat include methyl lithium, ethyl lithium, n-propyl lithium, n-butyl lithium, s-butyl lithium, t-butyl lithium or the like. These compounds can be used alone or in combination of two or more. Among these compounds, n-butyl lithium is preferable.

The used amount of the C1-6 alkyl magnesium halide is 0.25 to 2 mol, preferably 0.3 to 1.0 mol with respect to 1 mol of the compound represented by formula (VI). The used amount of the C1-6 alkyl lithium is 2.0 to 2.5 mol with respect to 1 mol of the C1-6 alkyl magnesium halide.

Next, the resulting reaction product reacts with trialkoxyborane reagent represented by $B(OR^{12})_3$ (in the formula, $R^{12}$ independently represents a C1-6 alkyl group, preferably a methyl group or i-propyl group). Thereby, a boronic acid derivative represented by formula (VIII) can be produced. This boronic acid derivative may be used as a production intermediate of the compound of the present invention. As for the trialkoxyborane reagent, one type may be used, or two or more types may be used in combination.

[Chemical formula 14]

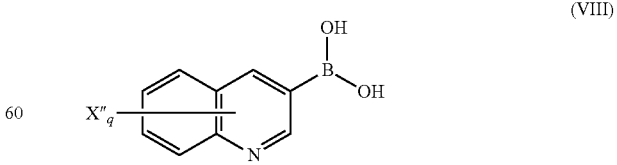

(VIII)

(in the formula, X" and q are the same as defiend above.)

The used amount of the trialkoxyborane reagent is 1.0 to 2.5 mol, preferably 1.0 to 1.2 mol with respect to the compound represented by formula (VI).

In the reaction, the alkyl magnesium halide and two times the number of moles thereof of alkyl lithium form an ate complex. This ate complex contributes to progression of the reaction. In this reaction, a method in which alkylmagnesium halide reacts with alkyllithium in advance to form an ate complex, followed by reacting with a compound represented by formula (VI), and then reacting with the trialkoxyborane reagent is preferable.

There are no particular limitations on the solvent used in this reaction as long as it does not inhibit the reaction. Examples of the solvent include hydrocarbon-based solvents such as hexane, cyclohexane, benzene or toluene, or ether-based solvents such as diethyl ether or THF. As for the solvent, only one type may be used, or two or more types may be used in combination.

Although there are no particular limitations on the amount of the solvent used, it is normally 3 to 100 parts by volume, preferably 4 to 40 parts by volume with respect to 1 part by weight of the compound represented by formula (VI).

The reaction temperature is preferably −78° C. to room temperature, more preferably −10 to 0° C.

In addition, a boronate ester derivative represented by formula (VIII') may also be used as a production intermediate of the compound of the present invention.

[Chemical formula 15]

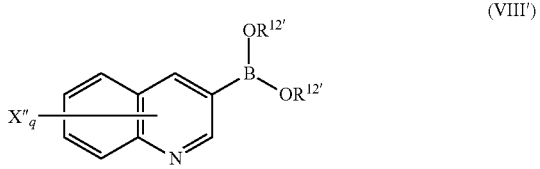

(VIII')

In formula (VIII'), X'' and q are the same as defined above. $R^{12'}$ independently represents a C1-8 alkyl group. $R^{12'}$ may bond together to form a 5- to 8-membered ring.

The boronate ester derivative represented by formula (VIII') may be produced by esterifying a boronic acid derivative represented by formula (VIII). As for the esterification method, the methods described in Non-Patent Document 5 and Non-Patent Document 6 may be used.

In either of these reactions, the target compound can be efficiently isolated by carrying out an ordinary post-treatment procedure used in the field of organic synthesis chemistry and a conventionally known separation and purification means as necessary following completion of the reaction.

The structure of the target compound can be identified and confirmed by measurement of $^1$H-NMR spectrum, IR spectrum or mass spectrum and elementary analysis or the like.

(Production Intermediate)

Examples of the production intermediate suitable for the present invention include a boronic acid derivative represented by formula (IX) or (X).

[Chemical formula 16]

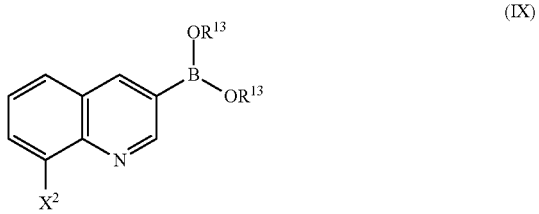

(IX)

In formula (IX), $X^2$ represents a fluorine atom or a chlorine atom. $R^{13}$ independently represents a hydrogen atom or a C1-8 alkyl group. The alkyl group represented by $R^{13}$ is preferably a methyl group or i-propyl group. $R^{13}$ and $R^{13}$ may bond to form a 5- to 8-membered ring.

This boronic acid derivative is particularly useful for the production intermediate of the compound of the present invention.

The boronic acid derivative represented by formula (IX) may be produced by the production method described above.

Examples of the boronic acid derivative represented by formula (IX) include the compounds shown in TABLE (1). In addition, in the table, Me represents a methyl group, $^i$Pr represents an i-propyl group.

TABLE 1

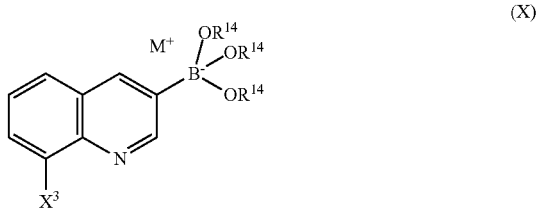

| Compound No. | $R^{13}$ | $R^{13'}$ | $X^2$ |
|---|---|---|---|
| C1-1 | H | H | F |
| C1-2 | H | H | Cl |
| C1-3 | Me | Me | F |
| C1-4 | Me | Me | Cl |
| C1-5 | $^i$Pr | $^i$Pr | F |
| C1-6 | —(CH$_2$)$_2$— | | F |
| C1-7 | —(CH$_2$)$_3$— | | F |
| C1-8 | —(CH$_2$)$_4$— | | F |
| C1-9 | —(CMe$_2$)$_2$— | | F |
| C1-10 | —(CMe$_2$)$_3$— | | F |

[Chemical formula 17]

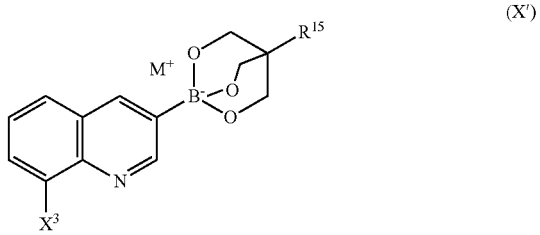

(X)

In formula (X), $X^3$ represents a hydrogen atom, a fluorine atom or a chlorine atom. $R^{14}$ independently represents a C1-8 alkyl group, preferably a C1-6 alkyl group, more preferably a methyl group, ethyl group, n-propyl group or i-propyl group. Two or more $R^{14}$s may bond to form a 5- to 8-membered ring. M represents an alkaline metal.

A compound in which three $R^{14}$ s bond to form a ring (boronic acid derivative represented by formula (X')) is more preferable.

[Chemical formula 18]

(X')

In formula (X'), $X^3$ represents a hydrogen atom, a fluorine atom or a chlorine atom. $R^{15}$ represents a C1-8 alkyl group, preferably a C1-6 alkyl group, more preferably a methyl group, ethyl group, n-propyl group or i-propyl group. M represents an alkaline metal.

The boronic acid derivative represented by formula (X') may be produced by the method described in Non-Patent Document 7 or the like.

Examples of the boronic acid derivative represented by formula (X') are shown in TABLE (2).

In the table, Et represents an ethyl group.

TABLE 2

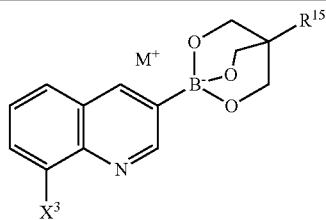

| Compound No. | $X^3$ | $R^{15}$ | M |
| --- | --- | --- | --- |
| C2-1 | F | H | K |
| C2-2 | F | Me | Li |
| C2-3 | F | Me | Na |
| C2-4 | F | Me | K |
| C2-5 | F | Et | K |
| C2-6 | Cl | H | K |
| C2-7 | Cl | Me | Li |
| C2-8 | Cl | Me | Na |
| C2-9 | Cl | Me | K |
| C2-10 | Cl | Et | K |
| C2-11 | H | Me | Na |
| C2-12 | H | Me | K |
| C2-13 | H | Et | K |

3) Fungicide for Agricultural and Horticultural Use

The fungicide of the present invention includes at least one selected from the compound of the present invention and salt thereof.

The fungicide of the present invention demonstrates superior fungicidal action against a wide range of types of fungi, such as fungi belonging to Oomycetes, Ascomycetes, Deuteromycetes or Basidiomycetes.

The fungicide of the present invention can be used to control various plant diseases occurring during cultivation of agricultural and horticultural crops including flowering plants, lawn grasses and pasture grasses by seed treatment, foliar spraying, soil application or water surface application and the like.

Examples of crops in which plant diseases can be controlled along with their plant diseases and causative organisms include:

Sugar Beets:
*Cercospora* leaf spot (*Cercospora beticola*)
*Aphanomyces* root rot (*Aphanomyces cochlloides*)
Root rot (*Thanatephorus cucumeris*)
Leaf blight (*Thanatephorus cucumeris*) or the like
Peanuts:
Brown leaf spot (*Mycosphaerella arachidis*)
Black leaf blight (*Mycosphaerella berkeleyi*) or the like
Cucumbers:
Powdery mildew (*Sphaerotheca fuliginea*)
Downy mildew (*Pseudoperonospora cubensis*)
Gummy stem blight (*Mycosphaerella melonis*)
*Fusarium* wilt (*Fusarium oxysporum*)
*Sclerotinia* rot (*Sclerotinia sclerotiorum*)
Gray mold (*Botrytis cinerea*)
Anthracnose (*Colletotrichum obriculare*)
Scab (*Cladosporium cucumerinum*)
*Corynespora* leaf spot (*Corynespora cassicola*)
Damping-off (*Pythium debaryanam*, *Rhizoctonia solani* Kuhn)
Bacterial spot (*Pseudomonas syringae* pv. *Lecrymans*) or the like
Tomatoes:
Gray mold (*Botrytis cinerea*)
Leaf mold (*Cladosporium fulvum*)
Late blight (*Phytophthora infestans*) or the like
Eggplants:
Gray mold (*Botrytis cinerea*)
Black rot (*Corynespora melongenae*)
Powdery mildew (*Erysiphe cichoracearum*)
Leaf mold (*Mycovellosiella nattrassii*) or the like
Strawberries:
Gray mold (*Botrytis cinerea*)
Powdery mildew (*Sphaerotheca humuli*)
Anthracnose (*Colletotrichum acutatum*, *Colletotrichum fragariae*)
*Phytophthora* rot (*Phytophthora cactorum*) or the like
Onions:
Neck rot (*Botrytis allii*)
Gray mold (*Botrytis cinerea*)
Leaf blight (*Botrytis squamosa*)
Downy mildew (*Peronospora destructor*)
Cabbage:
Clubroot (*Plasmodiophora brassicae*)
Bacterial soft rot (*Erwinia carotovora*)
Downy mildew (*Peronospora parasitica*) or the like
Kidney beans:
Stem rot (*Sclerotinia sclerotiorum*)
Gray mold (*Botrytis cinerea*) or the like
Apples:
Powdery mildew (*Podosphaera leucotricha*)
Scab (*Venturia inaequalis*)
Blossom blight (*Monilinia mali*)
Fruit spot (*Mycosphaerella pomi*)
*Valsa* canker (*Valsa mali*)
*Alternaria* blotch (*Alternaria mali*)
Rust (*Gymnosporangium yamadae*)
Ring rot (*Botryosphaeria berengeriana*)
Anthracnose (*Glomerella cingulata*, *Colletotrichum acutatum*)
Blotch (*Diplocarpon mali*)
Fly speck (*Zygophiala jamaicensis*)
Sooty blotch (*Gloeodes pomigena*) or the like
Persimmons:
Powdery mildew (*Phyllactinia kakicola*)
Anthracnose (*Gloeosporium kaki*)
Angular leaf spot (*Cercospora kaki*) or the like
Peaches:
Brown rot (*Monilinia fructicola*)
Scab (*Cladosporium carpophilum*)
*Phomopsis* rot (*Phomopsis* sp.) or the like
Cherries:
Brown rot (*Monlinia fructicola*) or the like
Grapes:
Gray mold (*Botrytis cinerea*)
Powdery mildew (*Uncinula necator*)
Ripe rot (*Glomerella cingulata*, *Colletotrichum acutatum*)
Downy mildew (*Plasmopara viticola*)
Anthracnose (*Elsinoe ampelina*)
Leaf blight (*Pseudocercospora vitis*)
Black rot (*Guignardia bidwellii*) or the like Pears:
Scab (*Venturia nashicola*)
Rust (*Gymnosporangium asiaticum*)
Black spot (*Alternaria kikuchiana*)
Ring rot (*Botryosphaeria berengeriana*)
Powdery mildew (*Phyllactinia mali*) or the like
Tea:
Gray blight (*Pestalotia theae*)
Anthracnose (*Collectotrichum theae-sinensis*) or the like
Citrus:
Scab (*Elsinoe fawcetti*)
Blue mold (*Penicillium italicum*)
Common green mold (*Penicillium digitatum*)
Gray mold (*Botrytis cinerea*)
Melanose (*Diaporthe citri*)
Canker (*Xanthomonas campestris* pv. *Citri*) or the like
Wheat:
Powdery mildew (*Erysiphe graminis* f. sp. *tritici*)
*Fusarium* blight (*Gibberella zeae*)
Leaf rust (*Puccinia recondita*)
Browning root rot (*Pythium iwayamai*)
Snow mold (*Monographella nivalis*)
Eye spot (*Pseudocercosporella herpotrichoides*)
Speckled leaf blotch (*Septoria tritici*)
Glume blotch (*Leptosphaeria nodorum*)
*Typhula* snow blight (*Typhula incarnata*)
*Sclerotinia* snow blight (*Myrioclerotinia borealis*)
Take-all (*Gaeumanomyces graminis*) or the like
Barley:
Stripe (*Pyrenophora graminea*)
Leaf blotch (*Rhynchosporium secalis*)
Loose smut (*Ustilago tritici, U. nuda*) or the like
Rice:
Blast (*Pyricularia oryzae*)
Sheath blight (*Rhizoctonia solani*)
Bakanae disease (*Gibberella fujikuroi*)
Brown spot (*Cochliobolus niyabeanus*)
Seedling blight (*Pythium graminicolum*)
Bacterial leaf blight (*Xanthomonas oryzae*)
Bacterial seedling blight (*Burkholderia plantarii*)
Bacterial brown stripe (*Acidovorax avanae*)
Bacterial grain rot (*Burkholderia glumae*) or the like
Tobacco:
*Sclerotinia* stem-rot (*Sclerotinia sclerotiorum*)
Powdery mildew (*Erysiphe cichoracearum*) or the like
Tulips:
Gray mold (*Botrytis cinerea*) or the like
Bent grass:
*Sclerotinia* snow blight (*Sclerotinia borealis*)
Bacterial shoot blight (*Pythium aphanidermatum*) or the like
Orchard grass:
Powdery mildew (*Erysiphe graminis*) or the like
Soybeans:
Purple stain (*Cercospora kikuchii*)
Downy mildew (*Peronospora Manshurica*)
*Phytophthora* root and stem rot (*Phytophthora sojae*) or the like
Potatoes, tomatoes:
Late blight (*Phytophthora infestans*) or the like In addition, the fungicide of the present invention has superior fungicidal effects against resistant orgamism.

Examples of the resistant orgamism include gray mold (*Botrytis cinerea*), sugar beet *cercospora* leaf spot (*Cercospora beticola*), apple scab (*Venturia inaequalis*) and pear scab (*Venturia nashicola*), which exhibit resistance to benzimidazole fungicides such as thiophanate-methyl, benomyl and carbendazim; gray mold (*Botrytis cinerea*) which exhibits resistance to dicarboximide fungicides (for example, vinclozolin, procymidone, iprodione) and the like.

Examples of diseases for which application of the fungicide of the present invention is more preferable include apple scab, cucumber gray mold, wheat powdery mildew, tomato late blight, wheat leaf rust, rice blast and cucumber *fusarium* wilt.

In addition, the fungicide of the present invention causes little chemical damage, exhibits low toxicity to fish and warm-blooded animals, and has a high degree of safety.

The fungicide of the present invention may be used in a form that can be adopted by an ordinary agricultural chemical for the purpose of using as an agricultural chemical, namely an agricultural chemical preparation such as a wettable powder, granules, powder, emulsion, aqueous solution, suspension, water-dispersible granules or the like.

Examples of additives and carriers used for solid formulations include vegetable powders such as soybean powder or wheat powder, mineral fine powders such as diatomaceous earth, apatite, gypsum, talc, bentonite, pyrophyllite or clay, and organic and inorganic compounds such as sodium benzoate, urea, sodium sulfate or the like.

Examples of solvents used for liquid formulations include kerosene, xylene and petroleum-based aromatic hydrocarbons, cyclohexane, cyclohexanone, dimethylformamide, dimethylsulfoxide, alcohol, acetone, trichloroethylene, methyl isobutyl ketone, mineral oil, vegetable oil, water and the like.

Moreover, a surfactant can be added to these preparations as necessary to obtain a uniform and stable form.

There are no particular limitations on the surfactants that can be added. Examples of the surfactant include nonionic surfactants such as polyoxyethylene-alkyl phenyl ethers, polyoxyethylene-alkyl ethers, polyoxyethylene-higher fatty acid esters, polyoxyethylene-sorbitan fatty acid esters or polyoxyethylene-tristyryl phenyl ether, and sulfuric acid ester salts of polyoxyethylene-alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates and isobutylene-maleic anhydrate copolymers.

Wettable powders, emulsions, flowable agents, aqueous solutions and water-dispersible granules obtained in this manner are used in the form of solutions, suspensions or emulsions by diluting to a prescribed concentration with water. In addition, powders and granules are used by spraying directly onto plants.

Normally, the amount of active ingredient in the fungicide of the present invention is preferably 0.01 to 90% by weight and more preferably 0.05 to 85% by weight based on the total weight of the preparation.

Although the applied amount of the fungicide of the present invention varies according to weather conditions, preparation form, application time, application method, applied location, target control disease, target crop and the like, it is normally 1 to 1,000 g and preferably 10 to 100 g as the amount of active ingredient compound per hectare.

In the case of applying by diluting a wettable powder, emulsion, suspension, aqueous solution or water-dispersible granules with water, the applied concentration is 1 to 1000 ppm and preferably 10 to 250 ppm.

The fungicide of the present invention can also be mixed with other types of fungicides, insecticides, miticides or synergists.

Typical examples of fungicides, insecticides, miticides and plant growth regulators that can be used by mixing with the fungicide of the present invention are indicated below.

Fungicides:

benzimidazole-based fungicides such as benomyl, carbendazim, fuberidazole, thiabendazole or thiophanate-methyl;

dicarboxylmide-based fungicides such as chlozolinate, iprodione, procymidone or vinclozolin;

DMI-fungicides such as imazalil, oxpoconazole, pefurazoate, prochloraz, triflumizole, triforine, pyrifenox, fenarimol, nuarimol, azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, etaconazole, furconazole-cis, ipconazole or imibenconazole;

phenylamide-based fungicides such as benalaxyl, furalaxyl, metalaxyl, metalaxyl-M, oxadixyl or ofurace;

amine-based fungicides such as aldimorph, dodemorph, fenpropimorph, tridemorph, fenpropidin, piperalin or spiroxamine;

phosphothioate-based fungicides such as EDDP, iprobenfos or pyrazophos;

dithiolane-based fungicides such as isoprothiolane;

carboxamide-based fungicides such as benodanil, boscalid, carboxin, fenfuram, flutolanil, furametpyr, mepronil, oxycarboxin, penthiopyrad or thifluzamide;

hydroxy-(2-amino)pyrimidine-based fungicides such as bupirimate, dimethirimol or ethirimol;

AP (anilinopyrimidine)-based fungicides such as cyprodinil, mepanipyrim or pyrimethanil;

N-phenylcarbamate-based fungicides such as diethofencarb;

QoI-based fungicides (Qo inhibitors) such as azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen or pyribencarb;

PP (phenylpyrrole)-based fungicides such as fenpiclonil or fludioxonil;

quinoline-based fungicides such as quinoxyfen;

AH (aromatic hydrocarbon)-based fungicides such as biphenyl, chloroneb, dicloran, quintozene, tecnazene or tolclofos-methyl;

MBI-R-based fungicides such as fthalide, pyroquilon or tricyclazole;

MBI-D-based fungicides such as carpropamid, diclocymet or fenoxanil;

SBI-based fungicides such as fenhexamid, pyributicarb or terbinafine;

phenylurea-based fungicides such as pencycuron;

QiI-based fungicides (Qi inhibitors) such as cyazofamid;

benzamide-based fungicides such as zoxamide;

enopyranuron-based fungicides such as blasticidin or mildiomycin;

hexopyranosyl-based fungicides such as kasugamycin;

glucopyranosyl-based fungicides such as streptomycin or validamycin;

cyanoacetoamide-based fungicides such as cymoxanil;

carbamate-based fungicides such as propamocarb, prothiocarb or polycarbamate;

uncoupling agent-based fungicides such as binapacryl, dinocap, ferimzone or fluazinam;

organic tin compound-based fungicides such as triphenyltin acetate, triphenyltin chloride or triphenyltin hydroxide;

phosphoric acid ester-based fungicides such as phosphorous acid, tolclofos-methyl or fosetyl;

phthalamic acid-based fungicides such as tecloftalam;

benzotriazine-based fungicides such as triazoxide;

benzenesulfonamide-based fungicides such as flusulfamide;

pyridazinone-based fungicides such as diclomezine;

CAA (carbonic acid amide)-based fungicides such as dimethomorph, flumorph, benthiavalicarb, iprovalicarb or mandipropamid;

tetracycline-based fungicides such as oxytetracycline;

thiocarbamate-based fungicides such as metasulfocarb; and fungicides based on other compounds such as etridiazole, polyoxin, oxolinic acid, hydroxyisoxazole, octhilinone, silthiofam, diflumetorim, acibenzolar-S-methyl, probenazole, tiadinil, ethaboxam, cyflufenamid, proquinazid, metrafenone, fluopicolide, copper hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine, anilazine, dithianon, chloropicrin, dazomet, metam sodium salt, qinomethionate, cyprofuram, silthiofam, agobacterium or fluoroimide.

Insecticides/Miticides:

Organic phosphorous and carbamate-based insecticides: fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemetone methyl, ethion, salithion, cyanophos, isoxathion, pyridafenthion, phosalone, methidathion, sulprofos, chlorfenvinphos, tetrachlorovinphos, dimethylvinphos, propaphos, isofenphos, ethyl thiometon, profenofos, pyraclofos, monocrotophos, azinphos-methyl, aldicarb, methomyl, thiodicarb, carbofuran, carbosulphan, benfuracarb, furathiocarb, propoXur, BPMC, MTMC, MIPC, carbaryl, pirimicarb, ethiophencarb, phenoxycarb, EDDP, and the like.

Pyrethroid-based insecticides: permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, flufenprox, acrinathrin, and the like.

Benzoylurea-based and other insecticides: diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, machine oil, BT and microbial agrichemicals such as insect pathogenic viruses.

Nematocides:

Fenamiphos, fosthiazate, and the like

Miticides:

Chlorobenzilate, phenisobromolate, dicofol, amitraz, BPPS, benzomate, hexythiazox, fenbutatin oxide, polynactin, chinomethionate, CPCBS, tetradifon, avermectin, milbemectin, clofentezine, cyhexatin, pyridaben, fenpyroximate, tebufenpyrad, pyrimidifen, fenothiocarb, dienochlor, and the like.

Plant growth regulators:

abscisic acid, indolebutyric acid, uniconazole, ethychlozate, ethephon, cloxyfonac, chlormequat, *chlorella* extract, calcium peroxide, cyanamide, dichlorprop, gibberellin, daminozide, decyl alcohol, trinexapac-ethyl, mepiquat chloride, paclobutrazol, paraffin, wax, piperonylbutoxide, pyraflufen-ethyl, flurprimidol, prohydrojasmon, prohexadione calcium salt, benzylaminopurine, pendimethalin, forchlorfenuron, maleic hydrazide potassium, 1-naphthylacetoamide, 4-CPA, MCPB, choline, oxyquinoline sulfate, ethychlozate, butoralin, 1-methylcyclopropene, aviglycine hydrochloride.

Although the following provides a more detailed explanation of the present invention by indicating examples thereof, the present invention is not limited to the following examples. Furthermore, compound numbers of the examples correspond to the compound numbers in the aforementioned tables.

Example 1

Synthesis of 4,4-dimethyl-1-(3-quinolinyl)-4,5-dihydro-3H-2-benzazepine (Compound no. B2-3)

(Step 1)

5 mL of phosphorous oxychloride and phosphorous pentachloride (0.33 g, 1.59 mmol) were added to 4,4-dimethyl-2,3,4,5-tetrahydro-1H-2-benzoazepin-1-one (0.30 g, 1.59 mmol) synthesized by referring to Non-Patent Documents 1 to 3 at room temperature. Then, the mixture was heated to reflux, and maintained for 5.5 hours. After cooling to room temperature, the mixture was concentrated under reduced pressure and the residue was poured into cool water. The aqueous layer was extracted with ethyl acetate (50 mL) and the organic layer was washed with water and saturated sodium bicarbonate water, followed by drying with magnesium sulfate. After filtering, the solvent was distilled off under reduced pressure to obtain a crude product of 1-chloro-4,4-dimethyl-2,3,4,5-tetrahydro-1H-2-benzoazepin-1-one. This crude product was used in the next reaction without purifying further.

(Step 2)

3-Quinoline boronic acid (0.22 g, 1.27 mmol) was dissolved in 20 mL of dimethylformamide, and cesium carbonate (1.23 g, 3.78 mol) and 2 mL of water were added to the resulting solution. After sparging with nitrogen gas, tetrakis(triphenylphosphine)palladium (0.30 g, 0.26 mmol) and all of the crude product of 1-chloro-4,4-dimethyl-2,3,4,5-tetrahydro-1H-2-benzoazepin-1-one obtained in Step 1 was added to the resulting solution. This solution was then heated to 90° C. with stirring for 14 hours. Subsequently, the reaction solution was cooled to room temperature followed by pouring in 50 mL of ethyl acetate and 50 mL of water and filtering over celite. The filtrate was extracted with 100 mL of ethyl acetate and the organic layer was washed with 50 mL of brine followed by drying with magnesium sulfate. After filtering, the solvent was distilled off under reduced pressure. The resulting residue was purified by silica gel column chromatography (hexan:ethyl acetate=2:1) to obtain the target compound (0.04, yield: 8.4%).

[Chemical formula 19]

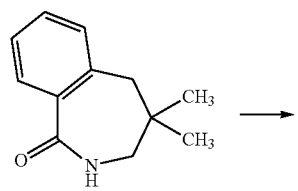

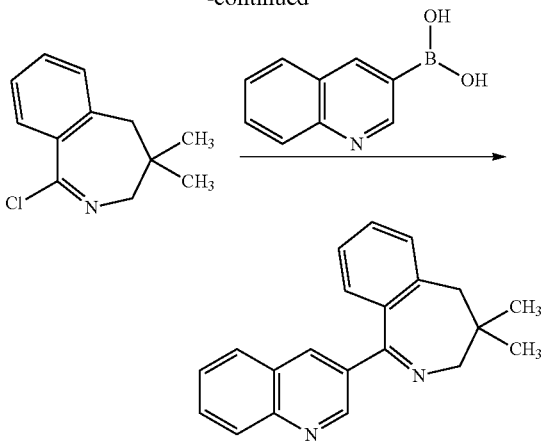

Example 2

Synthesis of 5,5-dimethyl-1-(3-quinolinyl)-4,5-dihydro-3H-2-benzazepine (Compound no. B2-25)

(Step 1)
5,5-Dimethyl-2,3,4,5-tetrahydro-1H-2-benzoazepin-1-one (4.0 g, 21.2 mmol) was dissolved in 100 mL of methylene chloride, followed by dropping trifluoromethanesulfonic acid anhydride (9.0 g, 31.7 mmol) while cooling to −10° C. and stirring for 1 hour at the same temperature. Moreover, 2,6-lutidine (3.4 g, 31.7 mmol) was added to the resulting reaction solution while cooling to −10° C. and stirred for 1 hour. Then, ice water was poured into the resulting reaction solution, followed by extracting with chloroform. The organic layer was washed with brine, and the solvent was distilled off under reduced pressure. The resulting residue was purified by silica gel column chromatography (eluent: benzene) to obtain trifluoromethanesulfonic acid 5,5-dimethyl-1-(3-quinolinyl)-4,5-dihydro-3H-2-benzoazepin-1-yl ester (1.38 g, yield: 20%).

(Step 2)
3-Quinoline boronic acid triol salt (compound no. C2-12) (0.46 g, 1.56 mmol) synthesized by the method of Example 9, trifluoromethanesulfonic acid 5,5-dimethyl-1-(3-quinolinyl)-4,5-dihydro-3H-2-benzoazepin-1-yl ester (0.5 g, 1.56 mmol) and tetrakistriphenyl phosphine palladium (0.86 g, 0.31 mmol) were added to 5 mL of toluene. After sparging with nitrogen gas, the resulting reaction solution was heated to reflux, and maintained for 14 hours. Then the reaction solution was cooled to room temperature and poured into ice water, followed by extracting with ethyl acetate. The organic layer was washed with brine, and the solvent was distilled off under reduced pressure. The resulting residue was purified by silica gel column chromatography (eluent: hexane:ethyl acetate=3:1) to obtain the target compound (0.06 g, yield: 13%).

[Chemical formula 20]

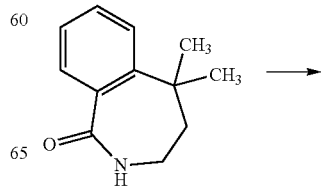

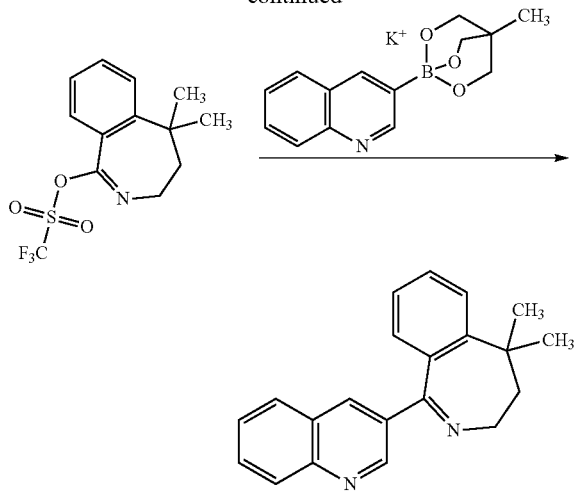

Example 3

Synthesis of 2,3-dihydro-5-(3-quinolinyl)-1H-1,4-benzodiazepine (compound no. B1-1)

3-(2-Bromobenzoyl)quinoline (10.30 g, 33.0 mmol) was added to 100 mL of ethylene diamine, followed by stirring at 100° C. for 18 hours. Then the resulting reaction solution was cooled to room temperature, and poured into brine, followed by extracting with ethyl acetate. The organic layer was washed with brine twice, followed by drying with magnesium sulfate. The solvent was distilled off under reduced pressure. The resulting residue was purified by silica gel column chromatography (eluent: chloroform:methanol=9:1) to obtain the target compound (1.19 g, yield: 13%).

[Chemical formula 21]

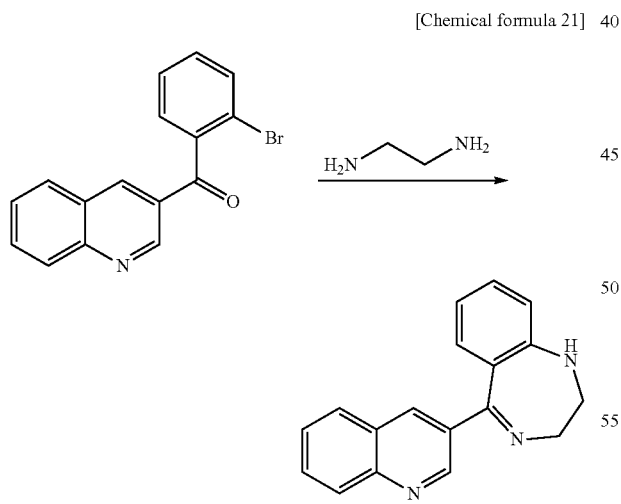

Example 4

Synthesis of 1-acetyl-2,3-dihydro-5-(3-quinolinyl)-1H-1,4-benzodiazepine (compound no. B1-13)

2,3-Dihydro-5-(3-quinolinyl)-1H-1,4-benzodiazepine (0.20 g, 0.73 mmol) was dissolved in 10 mL of methylene chloride, and acetic anhydride (0.1 mL, 1.1 mmol), pyridine (0.18 mL, 2.2 mmol) were added to the resulting solution, followed by stirring at room temperature for 2 hours. Then the resulting solution was distilled off under redused pressure for 14 hours. The resulting reaction solution was cooled to room temperature and added with ethyl acetate. Then the solution was washed with 0.5N citric acid solution, brine and saturated bicarbonate water, followed by drying with magnesium sulfate. The solvent was distilled off under reduced pressure. The resulting residue was purified by silica gel column chromatography (eluent: chloroform:methanol=9:1) to obtain the target compound (0.17 g, yield: 15%).

Example 5

Synthesis of 2,3-Dihydro-1-isopropyl-5-(3-quinolinyl)-1H-1,4-benzodiazepine (compound no. B1-37)

2,3-Dihydro-5-(3-quinolinyl)-1H-1,4-benzodiazepine (0.12 g, 0.44 mmol) was dissolved in 5 mL of dimethyl formamide, and added with isopropyl iodide (0.11 g, 0.65 mmol) and potassium carbonate (0.10 g, 0.72 mmol), followed by stirring at 100° C. for 48 hours. Isopropyl iodide (0.22 g, 1.29 mmol) and potassium carbonate (0.20 g, 1.45 mmol) were added to the resulting reaction solution, followed by stirring at 100° C. for 14 hours. The resulting reaction solution was cooled to room temperature, and cold water was poured into the reaction solution, followed by extracting with ethyl acetate. The organic layer was washed with brine, followed by drying magnesium sulfate. The solvent was distilled off under reduced pressure. The resulting residue was purified by silica gel column chromatography (chloroform:ethyl acetate=7:3) to obtain the target compound (0.012 g, yield: 8.7%).

Example 6

Synthesis of 5-(3-quinolinyl)-1,3-dihydro-2H-1,4-benzodiazepin-2-one (compound no. B4-1)

N-Boc-glycine (84.7 mg, 0.48 mmol) and EDCI HCl (92.6 mg, 0.48 mmol) were added to 6 mL of methylene chloride solution of (2-aminophenyl)-quinolin-3-yl-methanone (0.12 g, 0.48 mmol) under a nitrogen atmosphere at 0° C., followed by bringing back to room temperature and stirring for 45 hours. The resulting reaction solution was poured into 10 mL of ethyl acetate and 50 mL of water, and the aqueous layer was extracted with 100 mL of ethyl acetate, followed by washing the combined organic layer with 50 mL of brine and drying with magnesium sulfate. After filtering and concentrating, the resulting residue was purified by silica gel column chromatography to obtain {[2-(quinoline-3-carbonyl)-phenylcarbamoyl]-methyl}-carbamic acid tert-butyl ester (0.07 g, yield: 36%), which was slightly yellow amorphous. Moreover, 1 mL of trifluoroacetic acid was added to this compound, followed by stirring at room temperature for 16 hours. The resulting reaction solution was poured into a mixture of 10 mL of ethyl acetate, 50 mL of saturated sodium bicarbonate water and 50 mL of water, the aqueous layer was extracted with 100 mL of ethyl acetate, and the combined organic layer was washed with 50 mL of brine, followed by extracting with magnesium sulfate. After filtering and concentrating, the resulting residue was dissolved in 10 mL of ethanol, and 0.5 g of acetic acid was added to the resulting solution. The solution was heated to reflux, and maintained for 30 minutes. The reaction solution was poured into a mixture of 100 mL of ethyl acetate, 50 mL of saturated sodium bicarbonate water and 50 mL of water, and the aqueous layer was extracted with 100 mL of ethyl acetate. The combined organic layer was washed with 50 mL of brine, followed by drying with magnesium sulfate. After filtering and concentrating, the resulting residue was purified by silica gel column chromatography to obtain the target compound (0.03 g, yield: 61%), which was slightly yellow amorphous.

Example 7

Synthesis of 1-methyl-5-(3-quinolinyl)-1,3-dihydro-2H-1,4-benzodiazepin-2-one (compound no. B4-9)

60% sodium hydride (62.8 mg, 1.57 mmol) was added to 25 mL of THF solution of 5-(3-quinolinyl)-1,3-dihydro-2H-1,4-benzodiazepin-2-one (0.30 g, 1.04 mmol) at 0° C., followed by stirring at the same temperature for 20 minutes. Moreover, methyl iodide (0.18 g, 1.25 mmol) was added to the resulting solution, followed by bringing back to room temperature and stirring for 12 hours. 20 mL of water was slowly added to the reaction solution to stop the reaction. The resulting solution was extracted twice with 50 mL of ethyl acetate, and the extracted organic layers were mixed, followed by washing with 50 mL of brine and drying with magnesium sulfate. After filtering and concentrating, the resulting residue was purified by silica gel column chromatography to obtain the target compound (0.17 g, yield: 53%), which was slightly yellow amorphous.

Compounds produced by the methods described above are shown in TABLE (3) to TABLE (14). In the table, $^tBu$ represents a t-butyl group, Bn represents a benzyl group, $^iPr$ represents an i-propyl group, Ac represents an acetyl group, $^nPr$ represents an n-propyl group, Ph represents a phenyl group.

TABLE 3

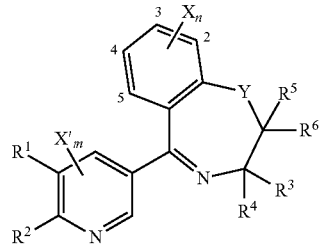

| Compound No. | $R^1$ | $R^2$ | $R^3$ | $R^4$ | $R^5$ | $R^6$ | Y | X'm | Xn |
|---|---|---|---|---|---|---|---|---|---|
| A1-1 | —(CH$_2$)$_4$— | | H | H | H | H | NH | — | — |
| A1-2 | —(CH$_2$)$_4$— | | Me | Me | H | H | NH | — | — |
| A1-3 | —(CH$_2$)$_4$— | | H | H | Me | Me | NH | — | — |
| A1-4 | —(CH$_2$)$_4$— | | Me | Me | Me | Me | NH | — | — |
| A1-5 | —(CH$_2$)$_4$— | | Cl | Cl | Cl | Cl | NH | — | — |
| A1-6 | —(CH$_2$)$_4$— | | H | H | —(CH$_2$)$_4$— | | NH | — | — |
| A1-7 | —(CH$_2$)$_4$— | | H | H | —(CH$_2$)$_5$— | | NH | — | — |
| A1-8 | —(CH$_2$)$_4$— | | —(CH$_2$)$_4$— | | H | H | NH | — | — |
| A1-9 | —(CH$_2$)$_4$— | | —(CH$_2$)$_5$— | | H | H | NH | — | — |
| A1-10 | H | H | H | H | Me | Me | NH | — | — |
| A1-11 | Me | Me | H | H | H | H | NH | — | — |
| A1-12 | Me | Me | H | H | Me | Me | NH | — | — |
| A1-13 | MeO | MeO | H | H | Me | Me | NH | — | — |
| A1-14 | CN | CN | H | H | Me | Me | NH | — | — |
| A1-15 | Cl | Cl | H | H | Me | Me | NH | — | — |
| A1-16 | CF$_3$ | CF$_3$ | H | H | Me | Me | NH | — | — |
| A1-17 | —(CH$_2$)$_4$— | | H | H | H | H | NAc | — | — |
| A1-18 | —(CH$_2$)$_4$— | | H | H | H | H | N—CO$_2$Me | — | — |
| A1-19 | —(CH$_2$)$_4$— | | H | H | H | H | N—CO$_2$$^tBu$ | — | — |
| A1-20 | —(CH$_2$)$_4$— | | H | H | H | H | NMe | — | — |
| A1-21 | —(CH$_2$)$_4$— | | H | H | H | H | NBn | — | — |
| A1-22 | —(CH$_2$)$_4$— | | H | H | Me | Me | NMe | — | — |
| A1-23 | —(CH$_2$)$_4$— | | H | H | Me | Me | N$^i$Pr | — | — |
| A1-24 | —(CH$_2$)$_3$— | | H | H | Me | Me | NH | — | — |
| A1-25 | —CH=CH—S— | | H | H | Me | Me | NH | — | — |
| A1-26 | —(CH$_2$)$_4$— | | H | H | H | H | CH$_2$ | — | — |
| A1-27 | —(CH$_2$)$_4$— | | Me | Me | H | H | CH$_2$ | — | — |
| A1-28 | —(CH$_2$)$_4$— | | H | H | Me | Me | CH$_2$ | — | — |
| A1-29 | —(CH$_2$)$_4$— | | Me | Me | Me | Me | CH$_2$ | — | — |
| A1-30 | —(CH$_2$)$_4$— | | Cl | Cl | Cl | Cl | CH$_2$ | — | — |
| A1-31 | —(CH$_2$)$_4$— | | H | H | —(CH$_2$)$_4$— | | CH$_2$ | — | — |
| A1-32 | —(CH$_2$)$_4$— | | H | H | —(CH$_2$)$_5$— | | CH$_2$ | — | — |
| A1-33 | H | H | H | H | Me | Me | CH$_2$ | — | — |
| A1-34 | Me | Me | H | H | H | H | CH$_2$ | — | — |
| A1-35 | Me | Me | H | H | Me | Me | CH$_2$ | — | — |
| A1-36 | —(CH$_2$)$_4$— | | H | H | Me | Me | CMe$_2$ | — | — |
| A1-37 | —(CH$_2$)$_4$— | | H | H | Me | Me | CEt$_2$ | — | — |
| A1-38 | —(CH$_2$)$_3$— | | H | H | Me | Me | CH$_2$ | — | — |

TABLE 4

| | | | | | | | | |
|---|---|---|---|---|---|---|---|---|
| A1-39 | —CH=CH—S— | H | H | Me | Me | $CH_2$ | — | — |
| A1-40 | —$(CH_2)_4$— | H | H | H | H | C(=O) | — | — |
| A1-41 | —$(CH_2)_4$— | Me | Me | H | H | C(=O) | — | — |
| A1-42 | —$(CH_2)_4$— | H | H | Me | Me | C(=O) | — | — |
| A1-43 | —$(CH_2)_4$— | Me | Me | Me | Me | C(=O) | — | — |
| A1-44 | —$(CH_2)_4$— | H | H | H | H | $SO_2$ | — | — |
| A1-45 | —$(CH_2)_4$— | Me | Me | H | H | $SO_2$ | — | — |
| A1-46 | —$(CH_2)_4$— | H | H | Me | Me | $SO_2$ | — | — |
| A1-47 | —$(CH_2)_4$— | Me | Me | Me | Me | $SO_2$ | — | — |
| A1-48 | —$(CH_2)_4$— | Cl | Cl | Cl | Cl | $SO_2$ | — | — |
| A1-49 | Me | Me | H | H | H | H | $SO_2$ | — | — |
| A1-50 | —$(CH_2)_4$— | —$(CH_2)_4$— | | H | H | $SO_2$ | — | — |
| A1-51 | —$(CH_2)_4$— | —$(CH_2)_5$— | | H | H | $SO_2$ | — | — |
| A1-52 | —$(CH_2)_4$— | H | H | Me | Me | $CH_2$ | — | 2-F |
| A1-53 | —CH=CH—S— | H | H | Me | Me | $CH_2$ | — | 2-F |
| A1-54 | Me | Me | H | H | Me | Me | $CH_2$ | — | 2-F |

TABLE 5

TABLE (4)

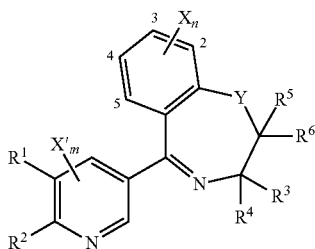

| Compound No. | $R^1$ | $R^2$ | $R^3$ | $R^4$ | $R^5$ | $R^6$ | Y | X'm | Xn |
|---|---|---|---|---|---|---|---|---|---|
| A2-1 | —$(CH_2)_4$— | | H | H | O | | NH | — | — |
| A2-2 | —$(CH_2)_4$— | | Me | Me | O | | NH | — | — |
| A2-3 | Me | Me | H | H | O | | NH | — | — |
| A2-4 | —$(CH_2)_4$— | | H | H | O | | NAc | — | — |
| A2-5 | —$(CH_2)_4$— | | H | H | O | | N—$CO_2$Me | — | — |
| A2-6 | —$(CH_2)_4$— | | H | H | O | | N—$CO_2^t$Bu | — | — |
| A2-7 | —$(CH_2)_4$— | | H | H | O | | N Me | — | — |
| A2-8 | —$(CH_2)_4$— | | H | H | O | | NBn | — | — |
| A2-9 | —$(CH_2)_4$— | | H | H | O | | $CH_2$ | — | — |
| A2-10 | —$(CH_2)_4$— | | Me | Me | O | | $CH_2$ | — | — |
| A2-11 | Me | Me | H | H | O | | $CH_2$ | — | — |
| A2-12 | —$(CH_2)_4$— | | H | H | O | | $SO_2$ | — | — |
| A2-13 | —$(CH_2)_4$— | | Me | Me | O | | $SO_2$ | — | — |
| A2-14 | Me | Me | H | H | O | | $SO_2$ | — | — |

TABLE 6

TABLE (5)

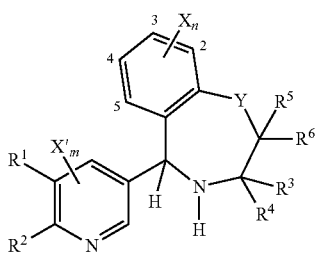

| Compound No. | $R^1$ | $R^2$ | $R^3$ | $R^4$ | $R^5$ | $R^6$ | Y | X'm | Xn |
|---|---|---|---|---|---|---|---|---|---|
| A3-1 | —$(CH_2)_4$— | | H | H | H | H | NH | — | — |
| A3-2 | —$(CH_2)_4$— | | Me | Me | H | H | NH | — | — |
| A3-3 | —$(CH_2)_4$— | | H | H | Me | Me | NH | — | — |
| A3-4 | —$(CH_2)_4$— | | Me | Me | Me | Me | NH | — | — |
| A3-5 | —$(CH_2)_4$— | | Cl | Cl | Cl | Cl | NH | — | — |
| A3-6 | —$(CH_2)_4$— | | H | H | —$(CH_2)_5$— | | NH | — | — |
| A3-7 | —$(CH_2)_4$— | | —$(CH_2)_5$— | | H | H | NH | — | — |
| A3-8 | H | H | H | H | Me | Me | NH | — | — |
| A3-9 | Me | Me | H | H | Me | Me | NH | — | — |
| A3-10 | MeO | MeO | H | H | Me | Me | NH | — | — |
| A3-11 | CN | CN | H | H | Me | Me | NH | — | — |
| A3-12 | Cl | Cl | H | H | Me | Me | NH | — | — |
| A3-13 | $CF_3$ | $CF_3$ | H | H | Me | Me | NH | — | — |
| A3-14 | —$(CH_2)_4$— | | H | H | H | H | NAc | — | — |
| A3-15 | —$(CH_2)_4$— | | H | H | Me | Me | NMe | — | — |

TABLE 7

| | | | | | | | | |
|---|---|---|---|---|---|---|---|---|
| A3-16 | —CH=CH—S— | H | H | Me | Me | NH | — | — |
| A3-17 | —$(CH_2)_4$— | | H | H | H | H | $CH_2$ | — | — |
| A3-18 | —$(CH_2)_4$— | | Me | Me | H | H | $CH_2$ | — | — |
| A3-19 | —$(CH_2)_4$— | | H | H | Me | Me | $CH_2$ | — | — |
| A3-20 | —$(CH_2)_4$— | | Me | Me | Me | Me | $CH_2$ | — | — |
| A3-21 | —$(CH_2)_4$— | | Cl | Cl | Cl | Cl | $CH_2$ | — | — |
| A3-22 | —$(CH_2)_4$— | | H | H | —$(CH_2)_5$— | | $CH_2$ | — | — |
| A3-23 | H | H | H | H | Me | Me | $CH_2$ | — | — |
| A3-24 | Me | Me | H | H | Me | Me | $CH_2$ | — | — |
| A3-25 | —$(CH_2)_4$— | | H | H | Me | Me | $CMe_2$ | — | — |
| A3-26 | —CH=CH—S— | H | H | Me | Me | $CH_2$ | — | — |
| A3-27 | —$(CH_2)_4$— | | H | H | H | H | C(=O) | — | — |
| A3-28 | —$(CH_2)_4$— | | Me | Me | H | H | C(=O) | — | — |
| A3-29 | —$(CH_2)_4$— | | H | H | Me | Me | C(=O) | — | — |
| A3-30 | —$(CH_2)_4$— | | Me | Me | Me | Me | C(=O) | — | — |
| A3-31 | —$(CH_2)_4$— | | H | H | H | H | $SO_2$ | — | — |
| A3-32 | —$(CH_2)_4$— | | Me | Me | H | H | $SO_2$ | — | — |

TABLE 7-continued

| | | | | | | | | |
|---|---|---|---|---|---|---|---|---|
| A3-33 | —(CH$_2$)$_4$— | H | H | Me | Me | SO$_2$ | — | — |
| A3-34 | —(CH$_2$)$_4$— | Me | Me | Me | Me | SO$_2$ | — | — |
| A3-35 | —(CH$_2$)$_4$— | Cl | Cl | Cl | Cl | SO$_2$ | — | — |
| A3-36 | Me | Me | H | H | H | H | SO$_2$ | — | — |
| A3-37 | —(CH$_2$)$_4$— | —(CH$_2$)$_5$— | H | H | SO$_2$ | — | — |

TABLE 8

TABLE (6)

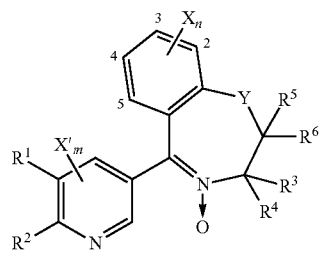

| Compound No. | R$^1$ | R$^2$ | R$^3$ | R$^4$ | R$^5$ | R$^6$ | Y | X'm | Xn |
|---|---|---|---|---|---|---|---|---|---|
| A4-1 | —(CH$_2$)$_4$— | | H | H | H | H | NH | — | — |
| A4-2 | —(CH$_2$)$_4$— | | Me | Me | H | H | NH | — | — |
| A4-3 | —(CH$_2$)$_4$— | | H | H | Me | Me | NH | — | — |
| A4-4 | —(CH$_2$)$_4$— | | Me | Me | Me | Me | NH | — | — |
| A4-5 | —(CH$_2$)$_4$— | | Cl | Cl | Cl | Cl | NH | — | — |
| A4-6 | —(CH$_2$)$_4$— | | H | H | —(CH$_2$)$_5$— | | NH | — | — |
| A4-7 | —(CH$_2$)$_4$— | | —(CH$_2$)$_5$— | | H | H | NH | — | — |
| A4-8 | H | H | H | H | Me | Me | NH | — | — |
| A4-9 | Me | Me | H | H | Me | Me | NH | — | — |
| A4-10 | MeO | MeO | H | H | Me | Me | NH | — | — |
| A4-11 | CN | CN | H | H | Me | Me | NH | — | — |
| A4-12 | Cl | Cl | H | H | Me | Me | NH | — | — |
| A4-13 | CF$_3$ | CF$_3$ | H | H | Me | Me | NH | — | — |
| A4-14 | —(CH$_2$)$_4$— | | H | H | H | H | NAc | — | — |
| A4-15 | —(CH$_2$)$_4$— | | H | H | H | H | N—CO$_2$Me | — | — |
| A4-16 | —(CH$_2$)$_4$— | | H | H | H | H | N—CO$_2$$^t$Bu | — | — |
| A4-17 | —(CH$_2$)$_4$— | | H | H | H | H | NMe | — | — |
| A4-18 | —(CH$_2$)$_4$— | | H | H | H | H | NBn | — | — |
| A4-19 | —(CH$_2$)$_4$— | | H | H | Me | Me | NMe | — | — |
| A4-20 | —CH=CH—S— | | H | H | Me | Me | NH | — | — |
| A4-21 | —(CH$_2$)$_4$— | | H | H | H | H | CH$_2$ | — | — |
| A4-22 | —(CH$_2$)$_4$— | | Me | Me | H | H | CH$_2$ | — | — |
| A4-23 | —(CH$_2$)$_4$— | | H | H | Me | Me | CH$_2$ | — | — |
| A4-24 | —(CH$_2$)$_4$— | | Me | Me | Me | Me | CH$_2$ | — | — |
| A4-25 | —(CH$_2$)$_4$— | | Cl | Cl | Cl | Cl | CH$_2$ | — | — |
| A4-26 | —(CH$_2$)$_4$— | | H | H | —(CH$_2$)$_5$— | | CH$_2$ | — | — |
| A4-27 | H | H | H | H | Me | Me | CH$_2$ | — | — |
| A4-28 | Me | Me | H | H | Me | Me | CH$_2$ | — | — |
| A4-29 | —(CH$_2$)$_4$— | | H | H | Me | Me | CMe$_2$ | — | — |
| A4-30 | —CH=CH—S— | | H | H | Me | Me | CH$_2$ | — | — |
| A4-31 | —(CH$_2$)$_4$— | | H | H | H | H | C(=O) | — | — |
| A4-32 | —(CH$_2$)$_4$— | | Me | Me | H | H | C(=O) | — | — |

TABLE 9

| | | | | | | | | |
|---|---|---|---|---|---|---|---|---|
| A4-33 | —(CH$_2$)$_4$— | H | H | Me | Me | C(=O) | — | — |
| A4-34 | —(CH$_2$)$_4$— | Me | Me | Me | Me | C(=O) | — | — |
| A4-35 | —(CH$_2$)$_4$— | H | H | H | H | SO$_2$ | — | — |
| A4-36 | —(CH$_2$)$_4$— | Me | Me | H | H | SO$_2$ | — | — |
| A4-37 | —(CH$_2$)$_4$— | H | H | Me | Me | SO$_2$ | — | — |
| A4-38 | —(CH$_2$)$_4$— | Me | Me | Me | Me | SO$_2$ | — | — |
| A4-39 | —(CH$_2$)$_4$— | Cl | Cl | Cl | Cl | SO$_2$ | — | — |
| A4-40 | Me | Me | H | H | H | H | SO$_2$ | — | — |
| A4-41 | —(CH$_2$)$_4$— | —(CH$_2$)$_5$— | H | H | SO$_2$ | — | — |

TABLE 10

TABLE (7)

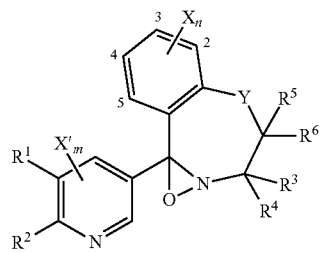

| Compound No. | R¹ | R² | R³ | R⁴ | R⁵ | R⁶ | Y | X'm | Xn |
|---|---|---|---|---|---|---|---|---|---|
| A5-1 | —(CH₂)₄— | | H | H | H | H | NH | — | — |
| A5-2 | —(CH₂)₄— | | Me | Me | H | H | NH | — | — |
| A5-3 | —(CH₂)₄— | | H | H | Me | Me | NH | — | — |
| A5-4 | —(CH₂)₄— | | Me | Me | Me | Me | NH | — | — |
| A5-5 | —(CH₂)₄— | | Cl | Cl | Cl | Cl | NH | — | — |
| A5-6 | —(CH₂)₄— | | H | H | —(CH₂)₅— | | NH | — | — |
| A5-7 | —(CH₂)₄— | | —(CH₂)₅— | | H | H | NH | — | — |
| A5-8 | H | H | H | H | Me | Me | NH | — | — |
| A5-9 | Me | Me | H | H | Me | Me | NH | — | — |
| A5-10 | MeO | MeO | H | H | Me | Me | NH | — | — |
| A5-11 | CN | CN | H | H | Me | Me | NH | — | — |
| A5-12 | Cl | Cl | H | H | Me | Me | NH | — | — |
| A5-13 | CF₃ | CF₃ | H | H | Me | Me | NH | — | — |
| A5-14 | —(CH₂)₄— | | H | H | H | H | NAc | — | — |
| A4-15 | —(CH₂)₄— | | H | H | H | H | N—CO₂Me | — | — |
| A4-16 | —(CH₂)₄— | | H | H | H | H | N—CO₂ᵗBu | — | — |
| A4-17 | —(CH₂)₄— | | H | H | H | H | NMe | — | — |
| A4-18 | —(CH₂)₄— | | H | H | H | H | NBn | — | — |
| A5-15 | —(CH₂)₄— | | H | H | Me | Me | NMe | — | — |
| A5-16 | —CH=CH—S— | | H | H | Me | Me | NH | — | — |
| A5-17 | —(CH₂)₄— | | H | H | H | H | CH₂ | — | — |
| A5-18 | —(CH₂)₄— | | Me | Me | H | H | CH₂ | — | — |
| A5-19 | —(CH₂)₄— | | H | H | Me | Me | CH₂ | — | — |
| A5-20 | —(CH₂)₄— | | Me | Me | Me | Me | CH₂ | — | — |

TABLE 11

| | | | | | | | | | |
|---|---|---|---|---|---|---|---|---|---|
| A5-21 | —(CH₂)₄— | | Cl | Cl | Cl | Cl | CH₂ | — | — |
| A5-22 | —(CH₂)₄— | | H | H | —(CH₂)₅— | | CH₂ | — | — |
| A5-23 | H | H | H | H | Me | Me | CH₂ | — | — |
| A5-24 | Me | Me | H | H | Me | Me | CH₂ | — | — |
| A5-25 | —(CH₂)₄— | | H | H | Me | Me | CMe₂ | — | — |
| A5-26 | —CH=CH—S— | | H | H | Me | Me | CH₂ | — | — |
| A5-27 | —(CH₂)₄— | | H | H | H | H | C(=O) | — | — |
| A5-28 | —(CH₂)₄— | | Me | Me | H | H | C(=O) | — | — |
| A5-29 | —(CH₂)₄— | | H | H | Me | Me | C(=O) | — | — |
| A5-30 | —(CH₂)₄— | | Me | Me | Me | Me | C(=O) | — | — |
| A5-31 | —(CH₂)₄— | | H | H | H | H | SO₂ | — | — |
| A5-32 | —(CH₂)₄— | | Me | Me | H | H | SO₂ | — | — |
| A5-33 | —(CH₂)₄— | | H | H | Me | Me | SO₂ | — | — |
| A5-34 | —(CH₂)₄— | | Me | Me | Me | Me | SO₂ | — | — |
| A5-35 | —(CH₂)₄— | | Cl | Cl | Cl | Cl | SO₂ | — | — |
| A5-36 | Me | Me | H | H | H | H | SO₂ | — | — |
| A5-37 | —(CH₂)₄— | | —(CH₂)₅— | | H | H | SO₂ | — | — |
| A5-38 | —(CH₂)₄— | | H | H | H | H | N—CO₂Me | — | — |
| A5-39 | —(CH₂)₄— | | H | H | H | H | N—CO₂tBu | — | — |
| A5-40 | —(CH₂)₄— | | H | H | H | H | NMe | — | — |
| A5-41 | —(CH₂)₄— | | H | H | H | H | NBn | — | — |

TABLE 12

TABLE (8)

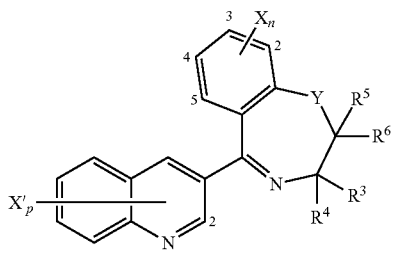

| Compound No. | R³ | R⁴ | R⁵ | R⁶ | Y | X'p | Xn |
|---|---|---|---|---|---|---|---|
| B1-1 | H | H | H | H | NH | — | — |
| B1-2 | Me | H | H | H | NH | — | — |
| B1-3 | Me | Me | H | H | NH | — | — |
| B1-4 | Et | Me | H | H | NH | — | — |
| B1-5 | ⁿPr | Me | H | H | NH | — | — |
| B1-6 | H | H | Me | Me | NH | — | — |
| B1-7 | Me | Me | Me | Me | NH | — | — |
| B1-8 | Cl | Cl | Cl | Cl | NH | — | — |
| B1-9 | H | H | H | H | NH | 5-F | — |
| B1-10 | H | H | H | H | NH | 6-F | — |
| B1-11 | —(CH₂)₄— | | H | H | NH | — | — |
| B1-12 | —(CH₂)₅— | | H | H | NH | — | — |
| B1-13 | H | H | H | H | NAc | — | — |
| B1-14 | H | H | H | H | N—CO₂Me | — | — |
| B1-15 | H | H | H | H | N—CO₂ᵗBu | — | — |
| B1-16 | H | H | H | H | NMe | — | — |
| B1-17 | H | H | H | H | NBn | — | — |
| B1-18 | H | H | Et | Me | NH | — | — |
| B1-19 | H | H | Et | Et | NH | — | — |
| B1-20 | H | H | Me | Me | NH | — | 2-Me |
| B1-21 | H | H | Me | Me | NH | — | 2-Cl |

TABLE 13

| Compound No. | R³ | R⁴ | R⁵ | R⁶ | Y | X'p | Xn |
|---|---|---|---|---|---|---|---|
| B1-22 | H | H | Me | Me | NH | — | 2-F |
| B1-23 | H | H | Me | Me | NH | — | 2-MeO |
| B1-24 | H | H | Me | Me | NH | — | 2-CF₃ |
| B1-25 | H | H | Me | Me | NH | 8-F | — |
| B1-26 | H | H | Me | Me | NH | 8-Me | — |
| B1-27 | H | H | Me | Me | NH | 8-Cl | — |
| B1-28 | H | H | Me | Me | NH | 8-F | 2-F |
| B1-29 | H | H | Me | Me | NH | 8-F | 2-Cl |
| B1-30 | H | H | Me | Me | NH | 8-Me | 2-Cl |
| B1-31 | H | H | Me | Me | NH | 8-Cl | 2-Cl |
| B1-32 | Me | Me | Me | Me | NH | — | 2-F |
| B1-33 | Me | Me | Me | Me | NH | 8-F | — |
| B1-34 | Me | Me | Me | Me | NH | 8-F | 2-F |
| B1-35 | H | H | H | H | NMe | — | 2-Cl |
| B1-36 | Me | Me | H | H | NH | — | 2-Cl |
| B1-37 | H | H | H | H | NⁱPr | — | — |
| B1-38 | H | H | H | H | NH | — | 2-Cl |
| B1-39 | H | H | H | H | N—C(=O)Ph | — | — |
| B1-40 | H | H | H | H | N—C(=O)H | — | — |
| B1-41 | Me | Me | H | H | NMe | — | — |
| B1-42 | H | H | Me | Me | NMe | — | — |
| B1-43 | H | H | Me | Me | NMe | — | 2-F |
| B1-44 | H | H | Me | Me | NMe | — | 2-Cl |
| B1-45 | H | H | Me | Me | N-allyl | — | 2-Cl |
| B1-46 | H | H | Me | Me | NBn | — | 2-Cl |
| B1-47 | H | H | Me | Me | NMe | 8-F | 2-F |
| B1-48 | Me | Me | H | H | NH | 8-F | 2-F |
| B1-49 | H | H | Me | Me | N-allyl | 8-F | 2-F |
| B1-50 | Me | Me | H | H | NMe | 8-F | 2-F |
| B1-51 | H | H | H | H | NH | 8-MeO | — |
| B1-52 | H | H | H | H | NH | 8-CF₃ | — |
| B1-53 | H | H | H | H | NH | — | 2-CN |
| B1-54 | H | H | H | H | NH | — | 2-NO₂ |
| B1-55 | H | H | H | H | NH | — | 2,3-F₂ |
| B1-56 | H | H | ᶜPr | H | NH | — | — |
| B1-57 | ᶜPr | H | H | H | NH | — | — |
| B1-58 | H | H | CF₃ | H | NH | — | — |
| B1-59 | CF₃ | H | H | H | NH | — | — |
| B1-60 | H | H | Ph | H | NH | — | — |
| B1-61 | Ph | H | H | H | NH | — | — |
| B1-62 | H | H | allyl | H | NH | — | — |
| B1-63 | allyl | H | H | H | NH | — | — |

TABLE 14

TABLE (9)

| Compound No. | R³ | R⁴ | R⁵ | R⁶ | Y | X'p | Xn |
|---|---|---|---|---|---|---|---|
| B2-1 | H | H | H | H | CH₂ | — | — |
| B2-2 | Me | Me | H | H | CH₂ | — | — |
| B2-3 | H | H | Me | Me | CH₂ | — | — |
| B2-4 | Me | Me | Me | Me | CH₂ | — | — |
| B2-5 | Cl | Cl | Cl | Cl | CH₂ | — | — |
| B2-6 | H | H | H | H | CH₂ | 5-F | — |
| B2-7 | H | H | H | H | CH₂ | 6-F | — |
| B2-8 | H | H | Et | Me | CH₂ | — | — |
| B2-9 | H | H | Et | Et | CH₂ | — | — |
| B2-10 | H | H | Me | Me | CH₂ | — | 2-Me |
| B2-11 | H | H | Me | Me | CH₂ | — | 2-Cl |
| B2-12 | H | H | Me | Me | CH₂ | — | 2-F |
| B2-13 | H | H | Me | Me | CH₂ | — | 2-MeO |
| B2-14 | H | H | Me | Me | CH₂ | — | 2-CF₃ |
| B2-15 | H | H | Me | Me | CH₂ | 8-F | — |
| B2-16 | H | H | Me | Me | CH₂ | 8-Me | — |
| B2-17 | H | H | Me | Me | CH₂ | 8-Cl | — |
| B2-18 | H | H | Me | Me | CH₂ | 8-F | 2-F |
| B2-19 | H | H | Me | Me | CH₂ | 8-F | 2-Cl |
| B2-20 | H | H | Me | Me | CH₂ | 8-Me | 2-Cl |
| B2-21 | H | H | Me | Me | CH₂ | 8-Cl | 2-Cl |
| B2-22 | Me | Me | Me | Me | CH₂ | — | 2-F |
| B2-23 | Me | Me | Me | Me | CH₂ | 8-F | — |
| B2-24 | Me | Me | Me | Me | CH₂ | 8-F | 2-F |
| B2-25 | H | H | H | H | CMe₂ | — | — |
| B2-26 | H | H | H | H | CMe₂ | 8-F | — |
| B2-27 | H | H | Me | Me | CMe₂ | — | — |
| B2-28 | H | H | H | H | CMe₂ | — | 2-F |
| B2-29 | H | H | H | H | CMe₂ | 8-F | 2-F |
| B2-30 | H | H | H | H | CMe₂ | — | 2-Cl |
| B2-31 | H | H | H | H | C(=O) | — | — |
| B2-32 | H | H | H | H | CMe₂ | 8-F | 2-Cl |

TABLE 15

TABLE (10)

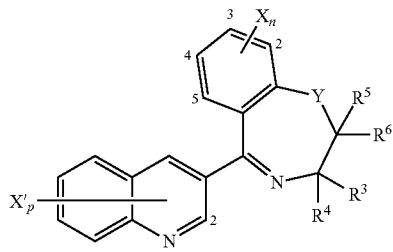

| Compound No. | R³ | R⁴ | R⁵ | R⁶ | Y | X'p | Xn |
|---|---|---|---|---|---|---|---|
| B3-1 | H | H | H | H | SO₂ | — | — |
| B3-2 | Me | H | H | H | SO₂ | — | — |
| B3-3 | Me | Me | H | H | SO₂ | — | — |
| B3-4 | Et | Me | H | H | SO₂ | — | — |
| B3-5 | ⁿPr | Me | H | H | SO₂ | — | — |
| B3-6 | H | H | Me | Me | SO₂ | — | — |
| B3-7 | H | H | Et | Me | SO₂ | — | — |
| B3-8 | H | H | ⁿPr | Me | SO₂ | — | — |
| B3-9 | Me | Me | Me | Me | SO₂ | — | — |
| B3-10 | Cl | Cl | Cl | Cl | SO₂ | — | — |
| B3-11 | H | H | H | H | SO₂ | 5-F | — |
| B3-12 | H | H | H | H | SO₂ | 6-F | — |
| B3-13 | H | H | H | H | SO₂ | 8-F | — |
| B3-14 | —(CH₂)₄— | | H | H | SO₂ | — | — |
| B3-15 | —(CH₂)₅— | | H | H | SO₂ | — | — |
| B3-16 | H | H | —(CH₂)₄— | | SO₂ | — | — |
| B3-17 | H | H | —(CH₂)₅— | | SO₂ | — | — |

TABLE 16

TABLE (11)

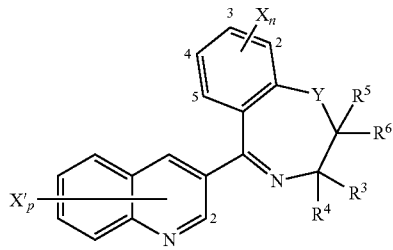

| Compound No. | R³ | R⁴ | R⁵ | R⁶ | Y | X'p | Xn |
|---|---|---|---|---|---|---|---|
| B4-1 | H | H | O | | NH | — | — |
| B4-2 | Me | Me | O | | NH | — | — |
| B4-3 | H | H | O | | NAc | — | — |
| B4-4 | H | H | O | | N—CO₂Me | — | — |
| B4-5 | H | H | O | | N—CO₂ᵗBu | — | — |
| B4-6 | H | H | O | | NMe | — | — |
| B4-7 | H | H | O | | NBn | — | — |
| B4-8 | H | H | O | | NH | 8-F | — |
| B4-9 | H | H | O | | NMe | — | — |
| B4-10 | H | H | O | | CH₂ | — | — |
| B4-11 | Me | Me | O | | CH₂ | — | — |
| B4-12 | H | H | O | | CH₂ | 8-F | — |
| B4-13 | H | H | O | | SO₂ | — | — |
| B4-14 | Me | Me | O | | SO₂ | — | — |
| B4-15 | H | H | O | | SO₂ | 8-F | — |

TABLE 17

TABLE (12)

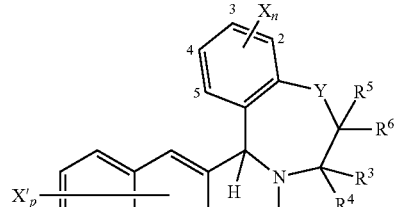

| Compound No. | R³ | R⁴ | R⁵ | R⁶ | Y | X'p | Xn |
|---|---|---|---|---|---|---|---|
| B6-1 | H | H | H | H | NH | — | — |
| B6-2 | Me | Me | H | H | NH | — | — |
| B6-3 | H | H | Me | Me | NH | — | — |
| B6-4 | Me | Me | Me | Me | NH | — | — |
| B6-5 | H | H | Me | Me | NH | — | 2-Cl |
| B6-6 | H | H | Me | Me | NH | — | 2-F |
| B6-7 | H | H | Me | Me | NH | 8-F | — |
| B6-8 | H | H | Me | Me | NH | 8-Me | — |
| B6-9 | H | H | Me | Me | NH | 8-Cl | — |
| B6-10 | H | H | Me | Me | NH | 8-F | 2-F |
| B6-11 | Me | Me | Me | Me | NH | — | 2-F |
| B6-12 | H | H | H | H | CH₂ | — | — |
| B6-13 | Me | Me | H | H | CH₂ | — | — |
| B6-14 | H | H | Me | Me | CH₂ | — | — |
| B6-15 | Me | Me | Me | Me | CH₂ | — | — |
| B6-16 | H | H | Me | Me | CH₂ | — | 2-Cl |
| B6-17 | H | H | Me | Me | CH₂ | — | 2-F |
| B6-18 | H | H | Me | Me | CH₂ | 8-F | — |
| B6-19 | H | H | Me | Me | CH₂ | 8-Me | — |
| B6-20 | H | H | Me | Me | CH₂ | 8-Cl | — |
| B6-21 | H | H | Me | Me | CH₂ | 8-F | 2-F |
| B6-22 | Me | Me | Me | Me | CH₂ | — | 2-F |
| B6-23 | H | H | H | H | SO₂ | — | — |
| B6-24 | Me | Me | H | H | SO₂ | — | — |
| B6-25 | H | H | Me | Me | SO₂ | — | — |
| B6-26 | H | H | Et | Me | SO₂ | — | — |
| B6-27 | H | H | ⁿPr | Me | SO₂ | — | — |
| B6-28 | Me | Me | Me | Me | SO₂ | — | — |
| B6-29 | H | H | Cl | Cl | SO₂ | — | — |
| B6-30 | H | H | H | H | SO₂ | 8-F | — |
| B6-31 | H | H | —(CH₂)₅— | | SO₂ | — | — |
| B6-32 | H | H | —(CH₂)₄— | | SO₂ | — | — |

TABLE 18

TABLE (13)

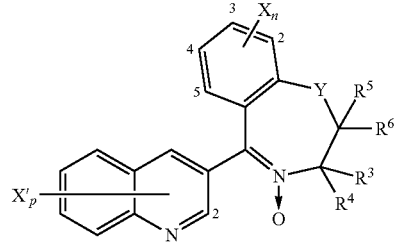

| Compound No. | R³ | R⁴ | R⁵ | R⁶ | Y | X'p | Xn |
|---|---|---|---|---|---|---|---|
| B7-1 | H | H | H | H | NH | — | — |
| B7-2 | Me | Me | H | H | NH | — | — |
| B7-3 | H | H | Me | Me | NH | — | — |
| B7-4 | Me | Me | Me | Me | NH | — | — |
| B7-5 | H | H | Me | Me | NH | — | 2-Cl |
| B7-6 | H | H | Me | Me | NH | — | 2-F |
| B7-7 | H | H | Me | Me | NH | 8-F | — |
| B7-8 | H | H | Me | Me | NH | 8-Me | — |

TABLE 18-continued

TABLE (13)

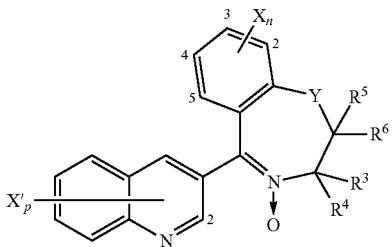

| Compound No. | R³ | R⁴ | R⁵ | R⁶ | Y | X'p | Xn |
|---|---|---|---|---|---|---|---|
| B7-9  | H  | H  | Me | Me | NH | 8-Cl | — |
| B7-10 | H  | H  | Me | Me | NH | 8-F  | 2-F |
| B7-11 | Me | Me | Me | Me | NH | —    | 2-F |
| B7-12 | H  | H  | H  | H  | NAc | — | — |
| B7-13 | H  | H  | H  | H  | N—CO₂Me | — | — |
| B7-14 | H  | H  | H  | H  | N—CO₂ᵗBu | — | — |
| B7-15 | H  | H  | H  | H  | NMe | — | — |

TABLE 19

| | | | | | | | |
|---|---|---|---|---|---|---|---|
| B7-16 | H  | H  | H  | H  | NBn | — | — |
| B7-17 | H  | H  | H  | H  | CH₂ | — | — |
| B7-18 | Me | Me | H  | H  | CH₂ | — | — |
| B7-19 | H  | H  | Me | Me | CH₂ | — | — |
| B7-20 | Me | Me | Me | Me | CH₂ | — | — |
| B7-21 | H  | H  | Me | Me | CH₂ | — | 2-Cl |
| B7-22 | H  | H  | Me | Me | CH₂ | — | 2-F |
| B7-23 | H  | H  | Me | Me | CH₂ | 8-F | — |
| B7-24 | H  | H  | Me | Me | CH₂ | 8-Me | — |
| B7-25 | H  | H  | Me | Me | CH₂ | 8-Cl | — |
| B7-26 | H  | H  | Me | Me | CH₂ | 8-F | 2-F |
| B7-27 | Me | Me | Me | Me | CH₂ | — | 2-F |
| B7-28 | H  | H  | H  | H  | SO₂ | — | — |
| B7-29 | Me | Me | H  | H  | SO₂ | — | — |
| B7-30 | H  | H  | Me | Me | SO₂ | — | — |
| B7-31 | H  | H  | Et | Me | SO₂ | — | — |
| B7-32 | H  | H  | ⁿPr | Me | SO₂ | — | — |
| B7-33 | Me | Me | Me | Me | SO₂ | — | — |
| B7-34 | H  | H  | Cl | Cl | SO₂ | — | — |
| B7-35 | H  | H  | H  | H  | SO₂ | 8-F | — |
| B7-36 | H  | H  | —(CH₂)₅— | | SO₂ | — | — |
| B7-37 | H  | H  | —(CH₂)₄— | | SO₂ | — | — |

TABLE 20

TABLE (14)

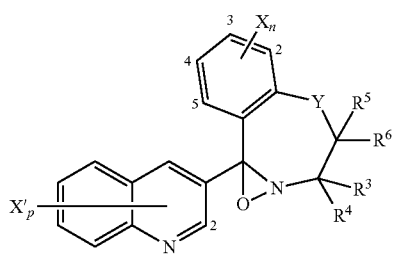

| Compound No. | R³ | R⁴ | R⁵ | R⁶ | Y | X'p | Xn |
|---|---|---|---|---|---|---|---|
| B8-1 | H  | H  | H  | H  | NH | — | — |
| B8-2 | Me | Me | H  | H  | NH | — | — |
| B8-3 | H  | H  | Me | Me | NH | — | — |
| B8-4 | Me | Me | Me | Me | NH | — | — |
| B8-5 | H  | H  | Me | Me | NH | — | 2-Cl |
| B8-6 | H  | H  | Me | Me | NH | — | 2-F |

TABLE 20-continued

TABLE (14)

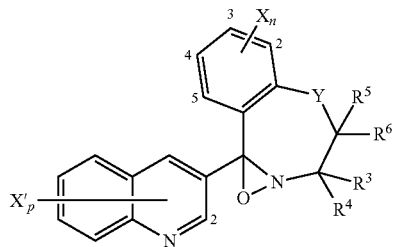

| Compound No. | R³ | R⁴ | R⁵ | R⁶ | Y | X'p | Xn |
|---|---|---|---|---|---|---|---|
| B8-7  | H  | H  | Me | Me | NH | 8-F | — |
| B8-8  | H  | H  | Me | Me | NH | 8-Me | — |
| B8-9  | H  | H  | Me | Me | NH | 8-Cl | — |
| B8-10 | H  | H  | Me | Me | NH | 8-F | 2-F |
| B8-11 | Me | Me | Me | Me | NH | — | 2-F |
| B8-12 | H  | H  | H  | H  | NAc | — | — |
| B8-13 | H  | H  | H  | H  | N—CO₂Me | — | — |
| B8-14 | H  | H  | H  | H  | N—CO₂ᵗBu | — | — |
| B8-15 | H  | H  | H  | H  | NMe | — | — |

TABLE 21

| | | | | | | | |
|---|---|---|---|---|---|---|---|
| B8-16 | H  | H  | H  | H  | NBn | — | — |
| B8-17 | H  | H  | H  | H  | CH₂ | — | — |
| B8-18 | Me | Me | H  | H  | CH₂ | — | — |
| B8-19 | H  | H  | Me | Me | CH₂ | — | — |
| B8-20 | Me | Me | Me | Me | CH₂ | — | — |
| B8-21 | H  | H  | Me | Me | CH₂ | — | 2-Cl |
| B8-22 | H  | H  | Me | Me | CH₂ | — | 2-F |
| B8-23 | H  | H  | Me | Me | CH₂ | 8-F | — |
| B8-24 | H  | H  | Me | Me | CH₂ | 8-Me | — |
| B8-25 | H  | H  | Me | Me | CH₂ | 8-Cl | — |
| B8-26 | H  | H  | Me | Me | CH₂ | 8-F | 2-F |
| B8-27 | Me | Me | Me | Me | CH₂ | — | 2-F |
| B8-28 | H  | H  | H  | H  | SO₂ | — | — |
| B8-29 | Me | Me | H  | H  | SO₂ | — | — |
| B8-30 | H  | H  | Me | Me | SO₂ | — | — |
| B8-31 | H  | H  | Et | Me | SO₂ | — | — |
| B8-32 | H  | H  | ⁿPr | Me | SO₂ | — | — |
| B8-33 | Me | Me | Me | Me | SO₂ | — | — |
| B8-34 | H  | H  | Cl | Cl | SO₂ | — | — |
| B8-35 | H  | H  | H  | H  | SO₂ | 8-F | — |
| B8-36 | H  | H  | —(CH₂)₅— | | SO₂ | — | — |
| B8-37 | H  | H  | —(CH₂)₄— | | SO₂ | — | — |

Physical properties and 1H-NMR data of some compounds produced in the aforementioned examples are shown in TABLE (15). The compound number described in TABLE (15) corresponds to the compound numbers described in the aforementioned tables.

TABLE 21

TABLE (15)

| Compound No. | Physical Property | ¹H NMR (300 MHz, CDCl³) δ |
|---|---|---|
| A1-52 | m.p. 110-113° C. | |
| A1-53 | amorphous | 1.14 (s, 6H), 2.47 (s, 2H), 3.19 (s, 2H), 6.95 (dd, 1H, J = 7.4, 1.2), 7.18 (m, 1H), 7.25-7.32 (m, 2H), 7.56 (d, 1H, J = 5.9 Hz), 8.31 (d, 1H, J = 2.4 Hz), 8.80 (d, 1H, J = 2.4 Hz) |
| A1-54 | nD20.5-1.5455 | |
| B1-1 | m.p. 201-202° C. | |
| B1-3 | m.p. 32-36° C. | |
| B1-6 | m.p. 133-136° C. | |
| B1-13 | m.p. 187-189° C. | |

TABLE 21-continued

TABLE (15)

| | Physical Property | $^1$H NMR (300 MHz, CDCl$^3$) δ |
|---|---|---|
| B1-16 | amorphous | 2.84 (s, 3H), 3.65-3.69 (m, 2H), 3.83-3.86 (m, 2H), 6.96 (t, 1H, J = 7.3 Hz), 7.03-7.07 (m, 2H), 7.41-7.47 (m, 1H), 7.51-7.57 (m, 1H), 7.71-7.77 (m, 1H), 7.79 (d, 1H, J = 7.8 Hz), 8.13 (d, 1H, J = 8.7 Hz), 8.22 (d, 1H, J = 2.1 Hz), 9.25 (d, 1H, J = 2.1 Hz) |
| B1-21 | m.p. 166-168° C. | |
| B1-22 | m.p. 130-134° C. | |
| B1-28 | m.p. 167-169° C. | |
| B1-35 | amorphous | 3.05 (s, 3H), 3.69-3.74 (m, 2H), 3.75-3.85 (m, 2H), 6.92 (dd, 1H, J = 7.7, 1.5 Hz), 7.03 (t 1H, J = 7.7 Hz), 7.44-7.84 (m, 4H), 8.15 (d, 1H, J = 8.6 Hz), 8.26 (d, 1H, J = 2.1 Hz), 9.26 (d, 1H, J = 2.1 Hz) |
| B1-36 | amorphous | 1.42 (s, 6H), 3.43 (d, J = 5.1 Hz, 2H), 5.62 (bs, 1H), 6.41 (t, 1H, J = 7.9 Hz), 6.97 (dd, 1H, J = 8.3, 1.5 Hz), 7.33 (dd, 1H, J = 7.7, 1.5 Hz), 7.50-7.85 (m, 3H), 8.12 (d, 1H, J = 8.3 Hz), 8.19 (d, 1H, J = 2.1 Hz), 8.96 (d, 1H, J = 2.1 Hz) |
| B1-37 | amorphous | 1.27 (d, 6H, J = 6.5 Hz), 3.60-3.75 (m, 2H), 3.85 (hep, 1H, J = 6.5 Hz), 3.89-3.95 (m, 2H), 6.87-6.91 (m, 1H), 6.98 (dd, 1H, J = 7.7, 1.5 Hz), 7.10 (d, 1H, J = 8.0 Hz), 7.34-7.84 (m, 4H), 8.13 (d, 1H, J = 8.6 Hz), 8.24 (d, 1H, J = 1.8 Hz), 9.20 (d, 1H, J = 2.1 Hz) |
| B1-38 | amorphous | 3.93-3.99 (m, 2H), 4.08-4.14 (m, 2H), 4.85 (bs, 1H), 6.64 (t, 1H, J = 7.9 Hz), 6.96 (dd, 1H, J = 7.9, 1.0 Hz), 7.40-7.84 (m, 4H), 8.12-8.16 (m, 1H), 8.23 (d, 1H, J = 1.6 Hz), 9.13 (d, 1H, J = 2.4 Hz) |
| B1-39 | m.p. 179-181° C. | |
| B1-40 | m.p. 157-158° C. | |
| B1-41 | amorphous | 1.40 (s, 6H), 3.12 (s, 3H), 3.38 (s, 2H), 6.45 (m, 1H), 6.87 (m, 1H), 7.07 (m, 1H), 7.30 (m, 1H), 7.54 (m, 1H), 7.70 (m, 1H), 7.80 (m, 1H), 8.10-8.13 (m, 2H), 8.93 (d, 1H, J = 2.1 Hz). |
| B1-42 | amorphous | 1.36 (s, 6H), 2.79 (s, 3H), 3.58 (s, 2H), 6.97-7.12 (m, 3H), 7.42 (m, 1H), 7.54 (m, 1H), 7.71-7.82 (m, 2H), 8.14 (d, 1H, J = 8.7 Hz), 8.28 (s, 1H), 9.24 (d, 1H, J = 2.1 Hz) |
| B1-43 | m.p. 120-123° C. | |
| B1-44 | m.p. 105-107° C. | |

TABLE 23

| B1-45 | m.p. 155-158° C. | |
|---|---|---|
| B1-46 | m.p. 155-157° C. | |
| B1-47 | m.p. 185-187° C. | |
| B1-48 | m.p. 42-45° C. | |
| B1-49 | m.p. 208-210° C. | |
| B1-50 | m.p. 145-148° C. | |
| B2-1 | amorphous | 2.39 (m, 2H), 2.67 (t, 2H, J = 7.1Hz), 3.53 (t, 2H, J = 6.5Hz), 7.1- 7.8 (m, 7H), 8.15 (dd, 1H, J = 8.5 0.9,Hz), 8.26 (d, 1H, J = 1.5 Hz), 9.33 (d, 1H, J = 2.2 Hz) |
| B2-3 | m.p. 115-116° C. | |
| B2-11 | amorphous | 1.17 (s, 6H), 2.65 (s, 2H), 3.23 (s, 2H), 7.07 (dd, 1H, J = 7.5, 0.9 Hz), 7.26 (m, 1H), 7.51- 7.58 (m, 2H), 7.73-7.81 (m, 2H), 8.15 (d, 1H, J = 8.1 Hz), 8.24 (d, 1H, J = 2.1 Hz), 9.28 (d, 1H, J = 2.1Hz) |
| B2-12 | amorphous | 1.54 (s, 6H), 2.48 (s, 2H), 3.23 (s, 2H), 6.97 (dd, 1H, J = 7.2, 1.2 Hz), 7.16-7.34 (m, 2H), 7.53-7.60 (m, 1H), 7.72-7.83 (m, 1H), 8.15 (d. 1H, J = 8.4 Hz), 8.26 (d, 1H, J = 1.5 Hz), 9.27 (d, 1H, J = 2.1 Hz) |

TABLE 23-continued

| B2-15 | m.p. 168-170° C. | |
|---|---|---|
| B2-18 | m.p. 183-185° C. | |
| B2-19 | m.p. 124-126° C. | |
| B2-25 | m.p. 121-123° C. | |
| B2-26 | amorphous | 1.36 (s, 6H), 2.30 (t, 2H, J = 6.5 Hz), 3.60 (t, 2H, J = 6.5 Hz), 7.09 (dd, 1H, J = 7.6, 1.3 Hz), 7.28-7.61 (m, 6H), 8.31 (t, 1H, J = 1.8 Hz), 9.31 (d, 1H, J = 2.1 Hz) |
| B2-27 | m.p. 187-189° C. | |
| B2-28 | amorphous | 1.48 (d, 6H, J = 5.1Hz), 2.29 (t, 2H, J = 6.4 Hz), 3.62 (t, 2H, J = 6.4 Hz), 6.88 (dd, 1H, J = 7.5, 1.5 Hz), 7.1-7.3 (m, 2H), 7.53-7.60 (m, 1H), 7.72-7.83 (m, 1H), 8.15 (d, 1H, J = 8.1 Hz), 8.24 (d, 1H, J = 1.8 Hz), 9.26 (d, 1H, J = 2.1 Hz) |
| B2-29 | amorphous | 1.47 (s, 3H), 1.49 (s. 3H), 2.29 (t, 2H, J = 6.3 Hz), 3.62 (t, J = 6.3 Hz, 2H), 6.86 (m, 1H), 7.12-7.27 (m, 2H), 7.41-7.63 (m, 3H), 8.28 (m, 1H), 9.28 (d, 1H, J = 1.8 Hz) |
| B2-30 | m.p. 145-146° C. | |
| B2-31 | m.p. 115-118° C. | |
| B2-32 | m.p. 166-168° C. | |
| B4-1 | amorphous | 4.44 (s, 2H), 7.18-7.26 (m, 2H), 7.37 (dd, 1H, J = 1.5, 7.8 Hz), 7.55-7.60 (m, 2H), 7.75-7.83 (m, 2H), 8.15 (d, 1H, J = 8.4 Hz), 8.26 (d, 1H, J = 1.8 Hz), 9.07 (bs, 1H), 9.16 (d, 1H, J = 2.1 Hz) |
| B4-9 | amorphous | 3.74 (s, 3H), 3.87 (d, 1H, J = 10.7 Hz), 4.93 (d, 1H, J = 10.7 Hz), 7.22-7.27 (m, 2H), 7.36 (dd, 1H, J = 1.5, 7.7 Hz), 7.43 (dd, 1H, J = 0.9, 8.3 Hz), 7.56-7.66 (m, 2H), 7.76-7.85 (m, 2H), 8.16 (d, 1H, J = 8.3 Hz), 8.34 (d, 1H, J = 2.1 Hz), 9.22 (d, 1H, J = 2.1 Hz). |
| B6-17 | m.p. 118-120° C. | |
| B7-22 | m.p. 98-102° C. | |
| B8-22 | m.p. 101-103° C. | |

(Production Intermediate Synthesis)

Example 8

8-Fluoro-3-quinoline boronic acid (Compound No. C1-1)

130 mL of an anhydrous THF solution was added to a 300 mL flask using a syringe after sparging with nitrogen gas followed by cooling the reaction container in a salt-ice bath. Subsequently, a THF solution of 0.91 M n-BuMgCl (20.72 mL, 18.86 mmol) and a hexane solution of 2.63 M n-BuLi (14.73 mL, 38.74 mmol) were sequentially added followed by stirring for 30 minutes at the same temperature. A solid form of 8-fluoro-3-iodoquinoline (13.92 g, 50.98 mmol) was added to this solution, and after stirring for 1.5 hours at the same temperature, trimethyl borate (6.36 g, 61.18 mmol) was added followed by additionally stirring for 2 hours. Water (27.8 g) and 1 M NaOH (27.8 g) were sequentially added to this reaction solution followed by stirring for 30 minutes at room temperature. The pH of the reaction solution was then adjusted to 6 to 7 using 1 M aqueous HCl solution, this solution was extracted twice with 300 mL of ethyl acetate. The extracted organic layers were combined and washed with brine (100 mL) followed by drying with magnesium sulfate. After filtering, the solvent was distilled off under reduced pressure. The resulting residue was sequentially washed with hexane and diethyl ether to obtain the target compound in the form of a beige solid (8.89 g, yield: 91%). The 8-fluoro-3-iodoquinoline used in the reaction was prepared with reference to the method described in the aforementioned Non-Patent Document 9 and Patent Document 3.

Physical properties: mp 198-201° C.

Example 9

3-Quinoline boronic acid triol salt (Compound No. C2-12)

8.65 g (50 mmol) of 3-quinoline boronic acid and 6.0 g (50 mmol) of 1,1,1-tris(hydroxymethyl)ethane were added to 50 mL of toluene followed by heating to reflux for 1 hour. After cooling the reaction liquid to 50° C., 2.66 g (47.5 mmol) of potassium hydroxide were gradually added followed by dehydrating with a Dean-Stark apparatus while further heating to reflux for 4 hours. After cooling the reaction liquid to room temperature, the precipitated crystals were filtered out and sequentially washed with 50 mL of toluene and 20 mL of acetone followed by drying for 12 hours under reduced pressure to obtain 10.4 g (yield: 71%) of the triol salt of the target compound.

$^1$H-NMR (300 MHz, DMSO) δ: 0.53 (s,3H), 3.66 (s,6H), 7.37-7.56 (m,2H), 7.73-7.85 (m,2H), 8.13 (s,1H), 8.83 (d,1H, J=1.5 Hz)

Example 10

Compound C2-4 was produced in the same manner.

$^1$H-NMR (300 MHz, DMSO) δ: 0.54 (s,3H), 3.69 (s,6H), 7.25-7.40 (m,2H), 7.56-7.59 (m,1H), 8.16 (s,1H), 8.93 (s,1H)

(Preparations)

Next, although the following indicates some examples of the fungicide of the present invention, the additives and addition ratios are not limited to these examples, but rather can be varied over a wide range. In addition, the term "parts" indicated in the preparation examples refers to parts by weight.

Preparation Example 1

Wettable Powder

| | |
|---|---|
| Compound of present invention | 40 parts |
| Clay | 48 parts |
| Sodium dioctylsulfosuccinate | 4 parts |
| Sodium lignin sulfonate | 8 parts |

The above components were uniformly mixed and finely crushed to obtain a wettable powder containing 40% of the active ingredient.

Preparation Example 2

Emulsion

| | |
|---|---|
| Compound of present invention | 10 parts |
| Solvesso 200 | 53 parts |
| Cyclohexanone | 26 parts |
| Calcium dodecylbenzenesulfonate | 1 part |
| Polyoxyethylene alkyl allyl ether | 10 parts |

The above components were mixed and dissolved to obtain an emulsion containing 10% of the active ingredient.

Preparation Example 3

Powder

| | |
|---|---|
| Compound of present invention | 10 parts |
| Clay | 90 parts |

The above components were uniformly mixed and finely crushed to obtain a powder containing 10% of the active ingredient:

Preparation Example 4

Granules

| | |
|---|---|
| Compound of present invention | 5 parts |
| Clay | 73 parts |
| Bentonite | 20 parts |
| Sodium dioctylsulfosuccinate | 1 part |
| Potassium phosphate | 1 part |

The above components were crushed and mixed well followed by the addition of water, mixing well, granulating and drying to obtain granules containing 5% of the active ingredient.

Preparation Example 5

Suspension

| | |
|---|---|
| Compound of present invention | 10 parts |
| Polyoxyethylene alkyl allyl ether | 4 parts |
| Sodium polycarbonate | 2 parts |
| Glycerin | 10 parts |
| Xanthan gum | 0.2 parts |
| Water | 73.8 parts |

The above components were mixed followed by wet-crushing to a particle diameter of 3 microns or less to obtain a suspension containing 10% of the active ingredient.

Preparation Example 6

Water-Dispersible Granules

| | |
|---|---|
| Compound of present invention | 40 parts |
| Clay | 36 parts |
| Potassium chloride | 10 parts |
| Sodium alkylbenzenesulfonate | 1 part |
| Sodium lignin sulfonate | 8 parts |
| Formaldehyde condensation product of Sodium alkybenzenesulfonate | 5 parts |

The above components were uniformly mixed and finely crushed followed by adding a suitable amount of water and mixing to form a clay-like mixture. The clay-like mixture was granulated and dried to obtain water-dispersible granules containing 40% of the active ingredient.

Test Example 1

Apple Scab Control Test

Emulsions of compounds of the present invention were sprayed at an active ingredient concentration of 100 ppm onto apple seedlings (variety: Rails Janet, leaf stage: 3 to 4) cultivated in unglazed pots. After allowing to air-dry at room temperature, the seedlings were inoculated with conidiospores of apple scab pathogen (Venturia inaequalis) followed by holding for 2 weeks indoors at 20° C. and high humidity using a 12 hour light/dark cycle. The appearance of lesions on the leaves was compared with untreated seedlings to determine control effects. The apple scab control test was carried out on compounds A1-52, A1-53, A1-54, B1-21, B1-22, B1-28, B1-35, B1-43, B1-44, B1-47, B1-50, B2-1, B2-3, B2-11, B2-12, B2-15, B2-18, B2-19, B2-25, B2-26, B2-27, B2-28, B2-29, B2-30, B2-32, B6-17, B7-22 and B8-22. As a result, the following compounds demonstrated control values of 75% or more:

Test Example 2

Cucumber Gray Mold Control Test

Emulsions of compounds of the present invention were sprayed at an active ingredient concentration of 100 ppm onto cucumber seedlings (variety: Sagami Hanjiro, leaf stage: cotyledon) cultivated in unglazed pots. After allowing to air-dry at room temperature, the seedlings were drip-inoculated with conidiospore suspensions of cucumber gray mold pathogen (*Botrytis cinerea*) followed by holding in the dark for 4 days indoors at 20° C. and high humidity. The appearance of lesions on the leaves was compared with untreated seedlings to determine control effects. The cucumber gray mold control test was carried on compounds A1-52, A1-53, A1-54, B1-6, B1-21, B1-22, B1-28, B1-36, B1-37, B1-38, B1-42, B1-43, B1-44, B1-45, B1-46, B1-47, B1-48, B1-49, B1-50, B2-1, B2-3, B2-11, B2-12, B2-15, B2-18, B2-19, B2-25, B2-26, B2-27, B2-28, B2-29, B2-30, B2-32, B6-17, B7-22 and B8-22. As a result, the following compounds demonstrated superior control values of 75% or more:

INDUSTRIAL APPLICABILITY

The nitrogen-containing heterocyclic compound or salt thereof of the present invention is a novel compound which is useful as an active ingredient of a fungicide for agricultural and horticultural use having an assured effect and being safely useable.

Furthermore, the fungicide for agricultural and horticultural use of the present invention has excellent control effect without causing drug-related problems in plants, and demonstrates less toxicity to humans, livestock or marine life and has less environmental impact.

Furthermore, the boronic acid derivative of the present invention is useful as an intermediate of the nitrogen-containing heterocyclic compound of the present invention or the like.

The invention claimed is:
1. A nitrogen-containing heterocyclic compound represented by formula (I) or salt thereof:

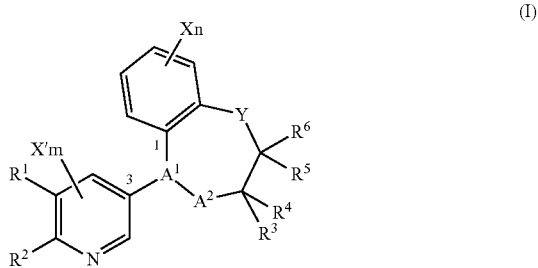

in formula (I), $R^1$ and $R^2$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino) C1-8 alkyl group, an optionally substituted hydroxy group, an optionally substituted amino group, an optionally substituted mercapto group, a substituted sulfonyl group, a halogeno group, a cyano group or a nitro group, or $R^1$ and $R^2$ bond to form an optionally substituted 5- to 8-membered ring together with the carbon atoms which bond to $R^1$ and $R^2$;

$R^3$ and $R^4$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterorcyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group, or $R^3$ and $R^4$ bond to form an oxo group, a thioxo group, an optionally substituted imino group or an optionally substituted exomethylene group;

$R^5$ and $R^6$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group, or R⁵ and R⁶ bond to form an oxo group, a thioxo group, an optionally substituted imino group or an optionally substituted exomethylene group;

partial structure A¹-A² in formula (I) represents any one of the following formulas (A) to (D):

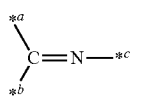

(A)

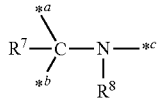

(B)

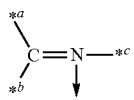

(C)

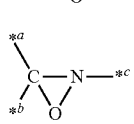

(D)

in each formula, *a represents bonding to the carbon atom at position 1 of the benzene ring;

*b represents bonding to the carbon atom at position 3 of the pyridine ring;

*c represents bonding to the carbon atom of CR³R⁴;

in formula (B), R⁷ represents a hydrogen atom, an optionally substituted C1-8 alkyl group, an optionally substituted C2-8 alkenyl group, an optionally substituted C2-8 alkynyl group, an optionally substituted C1-8 acyl group, an optionally substituted hydroxy group, an optionally substituted amino group, an optionally substituted mercapto group, a halogeno group or a cyano group;

in formula (B), R⁸ represents a hydrogen atom, an optionally substituted C1-8 alkyl group, an optionally substituted C2-8 alkenyl group, an optionally substituted C2-8 alkynyl group or an optionally substituted C1-8 acyl group;

Y represents a sulfonyl group, a group represented by NR⁹ or a group represented by CR¹⁰R¹¹;

R⁹ represents a hydrogen atom, an optionally substituted C1-8 alkyl group, an optionally substituted C2-8 alkenyl group, an optionally substituted C2-8 alkynyl group, an optionally substituted C1-8 acyl group, an optionally substituted (1-imino)C1-8 alkyl group or an optionally substituted amino group;

R¹⁰ and R¹¹ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group, or R¹⁰ and R¹¹ bond to form an oxo group, a thioxo group, an optionally substituted imino group or an optionally substituted exomethylene group;

wherein more than one group selected from R³ to R⁶ and R⁹ optionally bond to form an optionally substituted 3- to 8-membered ring together with the carbon atoms bonded thereto, or more than one group selected from R³ to R⁶ and R¹⁰ to R¹¹ optionally bond to form an optionally substituted 3- to 8-membered ring together with the carbons bonded thereto;

wherein not more than one of R³ and R⁴, R⁵ and R⁶, or R¹⁰ and R¹¹ bond to form an oxo group, a thioxo group, an optionally substituted imino group or an optionally substituted exomethylene group;

X and X' independently represent an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group, a cyano group or a nitro group;

m represents the number of X' and represents an integer of 0 to 2;

n represents the number of X and represents an integer of 0 to 4.

2. The nitrogen-containing heterocyclic compound or salt thereof according to claim 1, wherein
the nitrogen-containing heterocyclic compound is represented by formula (II)

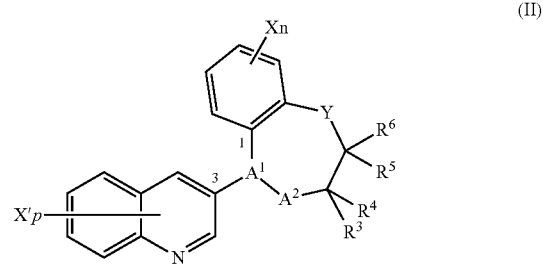

(II)

in formula (II),
p represents the number of X' and represents an integer of 0 to 6.

3. The nitrogen-containing heterocyclic compound or salt thereof according to claim 2, wherein
the nitrogen-containing heterocyclic compound is represented by formula (III)

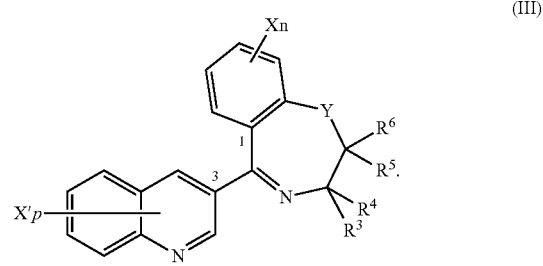

(III)

4. A fungicide for agricultural and horticultural use, comprising
the nitrogen-containing heterocyclic compound or salt thereof according to any one of claims 1 to 3 as an active ingredient.

5. The nitrogen-containing heterocyclic compound or salt thereof according to claim 2, wherein
in formula (II),
- $R^3$ and $R^4$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterorcyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group, or
- $R^3$ and $R^4$ bond to form an oxo group, a thioxo group, an optionally substituted imino group or an optionally substituted exomethylene group;
- $R^5$ and $R^6$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group, or
- $R^5$ and $R^6$ bond to form an oxo group, a thioxo group, an optionally substituted imino group or an optionally substituted exomethylene group;
- Y represents a sulfonyl group, a group represented by $NR^9$ or a group represented by $CR^{10}R11$;
- $R^9$ represents a hydrogen atom, an optionally substituted C1-8 alkyl group, an optionally substituted C2-8 alkenyl group, an optionally substituted C2-8 alkynyl group, an optionally substituted C1-8 acyl group, an optionally substituted (1-imino)C1-8 alkyl group or an optionally substituted amino group;
- $R^{10}$ and $R^{11}$ independently represent a hydrogen atom, an optionally substituted C1-8 alkyl group, an optionally substituted C2-8 alkenyl group, an optionally substituted C2-8 alkynyl group, an optionally substituted C3-8 cycloalkyl group, an optionally substituted C4-8 cycloalkenyl group, an optionally substituted C6-10 aryl group, an optionally substituted heterocyclic group, an optionally substituted C1-8 acyl group, an optionally substituted (1-imino)C1-8 alkyl group, an optionally substituted hydroxy group, an optionally substituted amino group, an optionally substituted mercapto group, a substituted sulfonyl group, a halogeno group or a cyano group, or
- $R^{10}$ and $R^{11}$ bond to form an oxo group, a thioxo group, an optionally substituted imino group or an optionally substituted exomethylene group.

* * * * *